US012584112B2

(12) United States Patent (10) Patent No.: US 12,584,112 B2
Lutolf et al. (45) Date of Patent: Mar. 24, 2026

(54) ORGANOID TISSUE ENGINEERING

(71) Applicant: ECOLE POLYTECHNIQUE FEDERALE DE LAUSANNE, Lausanne (CH)

(72) Inventors: Matthias Lutolf, Tolochenaz (CH); Nikolche Gjorevski, Renens (CH); Mike Nikolaev, Lausanne (CH); Sara Geraldo, Bussigny (CH); Nathalie Brandenberg, Lausanne (CH); Yoji Tabata, Cessy (FR)

(73) Assignee: Ecolepol Ytechnique Federale de Lausanne, Lausanne (CH)

( * ) Notice: Subject to any disclaimer, the term of this patent is extended or adjusted under 35 U.S.C. 154(b) by 272 days.

(21) Appl. No.: 16/462,313

(22) PCT Filed: Nov. 17, 2017

(86) PCT No.: PCT/EP2017/079651
§ 371 (c)(1),
(2) Date: May 20, 2019

(87) PCT Pub. No.: WO2018/091677
PCT Pub. Date: May 24, 2018

(65) Prior Publication Data
US 2019/0367872 A1 Dec. 5, 2019

(30) Foreign Application Priority Data
Nov. 18, 2016 (EP) ..................................... 16199677

(51) Int. Cl.
*C12N 5/071* (2010.01)
(52) U.S. Cl.
CPC .......... *C12N 5/068* (2013.01); *C12N 2501/11* (2013.01); *C12N 2501/155* (2013.01); *C12N 2501/415* (2013.01); *C12N 2506/23* (2013.01); *C12N 2513/00* (2013.01); *C12N 2533/54* (2013.01); *C12N 2533/90* (2013.01); *C12N 2535/10* (2013.01)
(58) Field of Classification Search
CPC ................ C12N 5/068; C12N 2501/11; C12N 2501/155; C12N 2501/415; C12N 2506/23; C12N 2513/00; C12N 2533/54; C12N 2533/90; C12N 2535/10; C12N 2535/00
See application file for complete search history.

(56) References Cited

U.S. PATENT DOCUMENTS

2006/0140914 A1* 6/2006 Jain ..................... A61L 27/3808
424/93.7
2012/0196312 A1 8/2012 Sato et al.
2015/0284689 A1* 10/2015 Nigam ................. C12N 5/0686
424/580

FOREIGN PATENT DOCUMENTS

CN 2271373 Y * 12/1997
WO 2014159356 A1 10/2014
WO 2016123474 A1 8/2016

OTHER PUBLICATIONS

McCracken KW, Howell JC, Wells JM, Spence JR. Generating human intestinal tissue from pluripotent stem cells in vitro. Nat Protoc. 2011;6(12):1920-1928. Published Nov. 10, 2011. (Year: 2011).*
Chen KG, Mallon BS, Mckay RD, Robey PG. Human pluripotent stem cell culture: considerations for maintenance, expansion, and therapeutics. Cell Stem Cell. 2014;14(1):13-26. (Year: 2014).*
Clevers H. Modeling Development and Disease with Organoids. Cell. Jun. 16, 2016; 165(7):1586-1597 (Year: 2016).*
Van der Sanden B, Dhobb M, Berger F, Wion D. Optimizing stem cell culture. J Cell Biochem. 2010;111(4):801-807. (Year: 2010).*
Lambshead JW, Meagher L, O'Brien C, Laslett AL. Defining synthetic surfaces for human pluripotent stem cell culture. Cell Regen. Nov. 22, 2013;2(1):7. (Year: 2013).*
Costello CM, Hongpeng J, Shaffiey S, Yu J, Jain NK, Hackam D, March JC. Synthetic small intestinal scaffolds for improved studies of intestinal differentiation. Biotechnol Bioeng. Jun. 2014;111(6):1222-32. (Year: 2014).*
Kretzschmar K, Clevers H. Organoids: Modeling Development and the Stem Cell Niche in a Dish. Dev Cell. Sep. 26, 2016;38(6):590-600. (Year: 2016).*
Chua CW, Shibata M, Lei M, Toivanen R, Barlow LJ, Bergren SK, Badani KK, McKiernan JM, Benson MC, Hibshoosh H, Shen MM. Single luminal epithelial progenitors can generate prostate organoids in culture. Nat Cell Biol. Oct. 2014;16(10):951-61, 1-4. (Year: 2014).*
Ranga et al. "Neural tube morphogenesis in synthetic 3D microenviron-ments."Proc Natl Acad Sci U S A . Nov. 1, 2016;113(44):E6831-E6839. Epub Oct. 14, 2016. (Year: 2016).*
Gin et al. "A model for cyst lumen expansion and size regulation via fluid secretion."J Theor Biol. Jun. 7, 2010;264(3):1077-88. (Year: 2010).*
Dunn et al. "Combined changes in Wnt signaling response and contact inhibition induce altered proliferation in radiation-treated intestinal crypts."Mol Biol Cell. Jun. 1, 2016; 27(11): 1863-1874. (Year: 2016).*
"What is a Subordinating Conjunction?" https://www.grammarly.com/blog/subordinating-conjunctions/#:~:text=The%20subordinating%20conjunction%20that%20is,t%20wear%20a%20seat%20belt. Acessed Feb. 7, 2023 (Year: 2023).*
Sciancalepore et al. "A bioartificial renal tubule device embedding human renal stem/progenitor cells. "PLoS One. Jan. 30, 2014;9(1):e87496. (Year: 2014).*

(Continued)

*Primary Examiner* — Titilayo Moloye
(74) *Attorney, Agent, or Firm* — Muncy, Geissler, Olds & Lowe, P.C.

(57) ABSTRACT

The invention relates to methods for developing and main-taining organoids and the organoids produced thereby.

10 Claims, 14 Drawing Sheets

(56)        References Cited

OTHER PUBLICATIONS

Sagrinati et al. "Isolation and characterization of multipotent progenitor cells from the Bowman's capsule of adult human kidneys." J Am Soc Nephrol.Sep. 2006;17(9):2443-56. (Year: 2006).*

Miya et al. "Enhancement of in vitro human tubulogenesis by endothelial cell-derived factors: implications for in vivo tubular regeneration after injury." Am J Physiol Renal Physiol. Aug. 2011;301(2):F387-95. (Year: 2011).*

Guney et al. "Epithelial-stromal cell interactions and extracellular matrix mechanics drive the formation of airway-mimetic tubular morphology in lung organoids." iScience. Aug. 30, 2021;24(9): 103061. (Year: 2021).*

International Search Report and Written Opinion dated Dec. 8, 2017 for corresponding International Patent Application No. PCT/EP2017/079651.

Gjorevski et al., "Designer matrices for intestinal stem cell and organoid culture", Nature, vol. 539, No. 7630, pp. 560-564, Nov. 16, 2016.

Toshiro Sato et al., "Single Lgr5 stem cells build crypt-villus structures in vitro without a mesenchymal niche", Nature, vol. 459, No. 7244, pp. 262-265, Mar. 29, 2009.

Yin Xiaolei et al., "Engineering stem cell organoids", Cell Stem Cell, vol. 18, No. 1, pp. 25-38, Jan. 7, 2016.

Akifumi Ootani et al., "Sustained in vitro intestinal epithelial culture within a Wnt-dependent stem cell niche", Nature Medicine, vol. 15, No. 6, pp. 701-706, Apr. 27, 2009.

Ying Chen et al., "Robust Bioengineered 3D functional human intestinal epithelium", Scientific Reports, vol. 5, Sep. 16, 2015.

* cited by examiner

F                                    G brightfield + Lgr5-GFP                    DAPI, Phalloidin

H

| Enterocytes | Goblet cells | Enteroendoctrine cells |
| the most numerous cells, nutrient absorption | secrete the mucas layer | <1% of the cells, secrete hormones |

DAPI, Phalloidin, L-FABP     DAPI, Phalloidin, Mucin     DAPI, Phalloidin, Chromogranin A I     Top Layer (z=0)          Inside crypt          Crypt bottom (z=60um)

K

A

B

ORGANOID TISSUE ENGINEERING

RELATED APPLICATIONS

The present application is a U.S. National Stage application under 35 USC 371 of PCT Application Serial No. PCT/EP2017/079651, filed on 17 Nov. 2017; which claims priority from EP Patent Application No. 16199677.2, filed 18 Nov. 2016, the entirety of all of which are incorporated herein by reference.

FIELD OF THE INVENTION

The invention relates to methods for developing and maintaining organoids and the organoids produced thereby.

BACKGROUND TO INVENTION

Two properties closely associated with stem cells are their ability to self-renew and give rise to specialized progeny. Research over the past two decades has also demonstrated that stem cells and their progeny possess an innate tendency to self-organize, thus giving rise to complex structures in a process reminiscent of those driving the development of tissues and organs. Embryoid bodies, aggregates of pluripotent stem cells that mimic aspects of early embryonic development and patterning, in part illustrate the self-organizing capacity of stem cells. This self-organizing potential, however, is perhaps best showcased by epithelial organoids, pluripotent or adult stem cell-derived three-dimensional (3D) structures that capture multiple histological and functional aspects of real organs with fidelity unmatched by previous in vitro models. Currently, organoid models of multiple organs, including the gut, stomach, colon, pancreas, retina, brain and kidney, have been established. The ability to generate organoids from adult or induced pluripotent human stem cells has afforded previously unimaginable possibilities for modeling human development and disease, drug discovery and personalized medicine. Furthermore, organoids promise to significantly advance the fields of tissue engineering and cell-based therapies, by serving as sources of highly organized and functional tissue for the repair of damaged or diseased organs.

Organoids can be formed in vitro by the proliferation and differentiation of tissue-specific cells within a 3D matrix scaffold. Attempts have been made to increase the relevance of organoids as in vitro tissue models by restricting their growth. In particular, scaffolds have been developed that model the geometrical shape of particular tissues, such as the intestinal villi. Differentiation of cells within these scaffolds has met with varied success.

Gastrointestinal organoids display a particularly high level of multicellular organization and a wide range of applications, including as models of the intestinal stem cell (ISC) niche, models of intestinal development and disease, platforms for drug screening and personalized medicine and sources of transplantable tissue for clinical use. However, the process of intestinal organoid formation is largely stochastic and the resulting structures differ from the native organ in multiple aspects. Notably, the location, size and number of crypt-like domains cannot be controlled, whereas villus structures are absent altogether. Furthermore, the mechanisms that underlie the patterning and self-organization of these structures in the absence of a mesenchymal compartment are not fully understood.

As described below, there have been a number of attempts at growing organoids within or on scaffolds mirroring in vivo tissue structure.

Costello et al. (Costello et al., 2014) provides synthetic 3D hydrogel scaffolds for supporting growth of intestinal epithelial cell lines (Caco-2 cells and HT29-MTX) and isolated crypt cells from the mouse small intestine. The scaffolds are formed from porous poly Lactic-co-Glycolic Acid (PLGA) using an agarose mould of a villus array (Costello et al., FIG. 1). Isolated crypt cells seeded into these scaffolds differentiate to form a spatial arrangement of Paneth cells, goblet cells, and enterocytes (page 1230, column 1, paragraph 1). This method relies on either a starter culture containing the multiple cell types present in an isolated crypt, or the proliferation and spontaneous differentiation capabilities of epithelial cell lines.

Chen et al. (Chen et al., 2015) describes the growth of the intestinal epithelial cell lines Caco-2 cells and HT29-MTX and primary human intestinal myofibroblasts (H-InMyoFibs) on the surface of silk based porous scaffolds. The scaffolds are tubular shaped, with or without an internal screw pattern. Caco-2 cells and HT29-MTX cells grown on the scaffolds in the presence of H-InMyoFibs form polarized columnar structures. This method is therefore also reliant on epithelial cell lines.

Levin et al. (Levin et al., 2013) describes the use of synthetic scaffolds formed from cylinders of non-woven poly-glycolic acid sealed with poly-L-lactic acid and coated with collagen (page 131, paragraph 2). In this method, organoids isolated from intestinal tissue are loaded onto the scaffold and directly implanted into an animal subject (page 131, paragraph 3). Levin therefore does not provide a method for growing organoids in vitro.

Finkbeiner et al. (Finkbeiner et al., 2015) provides scaffolds formed from decellularized small intestine (Finkbeiner et al., FIG. 1B). These native scaffolds are re-seeded with human intestine organoids, cultured in vitro and then transplanted into a immune-compromised mouse. Finkbeiner also provides a synthetic polyglycolic acid/collagen scaffold, on to which organoids are seeded and the scaffold then immediately implanted into a mouse (Finkbeiner et al., FIG. 10). The authors show that the synthetic scaffolds can support organoid survival differentiation in vivo but not in vitro, whilst decellularized small intestine scaffolds support organoid survival, but do not provide the necessary cues for stem cell differentiation (Finkbeiner et al., FIGS. 3C and 3D). Finkbeiner therefore does not provide a method for growing and maintaining organoids on scaffolds in vitro.

JP 2014/138605, (Mongens et al., 2014) describes a method for growing stem cells in structures of biocompatible materials having defined surface topographies (paragraph [0018]) such as a surface covered in micro-projections. The structures are selected to promote growth of undifferentiated stem cells (paragraph [0025]) and/or large-scale and uniform differentiation of stem cells (paragraphs [0029] and [0051]), primarily by providing a greater surface area for cell-adhesion. The differentiated cells can then be harvested and used in a variety of applications. The methods disclosed by Mongens are therefore not applicable to the field of organoids, as the purpose of Mongens is to avoid morphogenesis, and instead promote uniform growth or differentiation.

A number of recent studies have demonstrated the growth of organoids in vitro within microwells. However, the structures of the organoids are not restricted by the size or shape of the microwells:

Todhunter et al. (Todhunter et al., 2015) describes arrays of cells embedded in position by DNA-programmed assembly. The cells are first functionalized by incorporation of DNA oligonucleotides into their cell membranes and then attached to glass slides via interaction of these oligonucleotides with complementary sequences within DNA spots fixed to the glass. Multiple rounds of cell adhesion lead to the formation of 3D micro-tissue structures around the spots. A hydrogel is allowed to form around the fixed cell in order to embed them in position.

US 2011/0171712 (Rivron et al., 2011) describes the growth of cell aggregates within the confinement of a micro-array plate. The aggregates are formed by applying a cell suspension on top of a microwell array and allowing the cells to settle in the microarrays. Upon spatial confinement in the wells, the cells aggregate spontaneously (column 5, paragraph 4-5). The aggregates may vary in shape, and may for example form spheres, cylinders, rods or cubes (column 2, paragraph [0021]). The confined aggregates are then harvested from the microwells, combined and transferred to a seeding surface scaffold for assembly into tissue constructs (page 4, paragraphs [0037]), wherein the topography and patterning of the surface may govern this assembly process (page 4, paragraph [0038]). The tissue constructs are then induced to undergo morphogenesis, a process that may be governed by mechanical constraints (page 4, paragraph [0042]). Particularly, a biomaterial may be used as a scaffold that provides mechanical support or assists in achieving a particular desired shape (page 5, paragraph [0048]). The methods of Rivron therefore require generation of pre-formed tissue aggregates that must be harvested and combined in order to produce tissues.

Restricted growth of epithelial cells within micro-cavities has also been described. Nelson et al. (Nelson et al., 2006) discloses the production of engineered epithelial tubes from primary cells or cells of an epithelial cell line embedded in the tubular cavities of a collagen gel. When stimulated with growth factors, including EGF and HGF, the tubes extend branches into the surrounding collagen matrix. The tubular cavities are not used to produce organoids with a particular shape from stem cells. Moreover, in the present work, the shape of the micro-cavities is not shown to pattern stem cell fate, which is key for organoid development, WO 2016/123474 A1 (to The University of North Carolina at Chapel Hill) describes the use of geometry as a support and stem cell patterning is done via gradients of soluble factors. Moreover, this work mentions numerous times explicitly that without gradients the stem cells do not localize in the bottom of the micro-cavity and thus shape is not the driver of organoid morphogenesis in the presented system.

Therefore, there is a need in the field for a reliable method of producing organoids in vitro from stem cells or tumour cells that accurately reflect tissue morphology in vivo.

SUMMARY OF INVENTION

The inventors provide a method for obtaining an organoid having a pre-determined shape, comprising seeding one or more self-renewing cells onto a surface having a 3D structure, culturing the seeded cells under self-renewal conditions such that the cells proliferate to form a colony having the same 3D shape as the features of the surface, and culturing the colony under differentiation conditions such that the colony undergoes morphogenesis to form an organoid. The inventors made the surprising discovery that the geometry of a colony of proliferating epithelial cells provides sufficient information to the cells to direct subsequent morphogenesis of the colony into an organoid having a tissue shape representative of the in vivo tissue. This discovery provides the basis of a method of growing organoids in situ on a scaffold from one or more self-renewing cells. The scaffold determines the shape of the colony, which in turn determines the shape and the patterning of the resultant organoid formed when the colony is subjected to differentiation conditions. The same scaffold structure can therefore be used to produce organoids with highly reproducible shapes and patterning (i.e. the same shape and patterning can be repeatedly produced using scaffolds with the same structure) wherein the shape and patterning of an organoid is pre-determined by the scaffold structure.

Significantly, the present invention involves culturing cells on a surface with a 3D structure (for example, wells, cavities, or other culture vessels) such that cells form an organoid having a pre-determined patterning and tissue shape. The present inventors have determined that the control of geometry itself determines cell fate patterning and consequently the induction of morphogenesis, which then permits organoid formation in a repeatable and reliable manner.

The present process differs from cell culture within a 3D matrix, not least in that such prior art methods do not represent culture on a surface having a 3D structure, but rather represent culture within a 3D isotropic environment. The 3D matrix does not in itself constrain cells and organoid growth to a specific, repeatable 3D shape, but merely provides an appropriate environment within which cells can grow. Organoids produced by some of the methods described herein are not grown within a 3D scaffold or matrix (or at least, are not grown solely within a 3D scaffold or matrix without additional spatial constraints), but rather are grown on a surface having a 3D structure.

Furthermore, this process differs from prior art methods such as use microcavities and microwells as a means to aggregate and/or contain the organoids. In the discussed prior art methods, a 3D scaffold is used solely as a fixed support for 3D cell culture. This makes the final tissue shape strictly predefined by the initial geometry, rather than allowing spatial cell patterning by the initial shape, which then guides the subsequent morphogenesis to form an organoid with reproducible and predictable morphological features, as in the present invention.

The present invention seeks to overcome these and other disadvantages of the art.

Using the methods of the invention, the inventors have also determined a fundamental mechanism of pattern formation that may contribute toward intestinal development in vivo.

ABBREVIATIONS 2D two dimensional
3D three-dimensional
96U 96 well U-bottom plates
CFTR cystic fibrosis transmembrane conductance regulator
DHM digital holographic microscopy
ECM extracellular matrix
EGFP enhanced green fluorescence protein
GFP green fluorescence protein
ISC Intestinal stem cells
MW microwells
NEAA non-essential amino acids
PDMS polydimethylsiloxane ROI region of interest RT-qPCR Real time quantitative polymerase chain reaction

DETAILED DESCRIPTION

(A) Arrays of dissociated ISCs confined within hydrogel cavities of controlled geometry are generated through a combination of photolithography and micro-moulding. (B) Self-organization of dissociated ISCs into a lumenized intestinal tubule of controlled geometry. (C) The same process can be used to generate tubular tissues of varying lengths, and tissues of other geometries, such as circles. (D) Lgr5-EGFP within a tissue formed by culturing ISCs in expansion medium for two days. (E) Lgr5-EGFP within a tissue formed by culturing ISCs in expansion medium for two days, and cultured in organoid formation medium for an additional two days. Organoids formed by engineered intestinal tissues stained for (F) lysozyme and (G) mucin-2. Scale bars, 50 μm.

Figure 2:
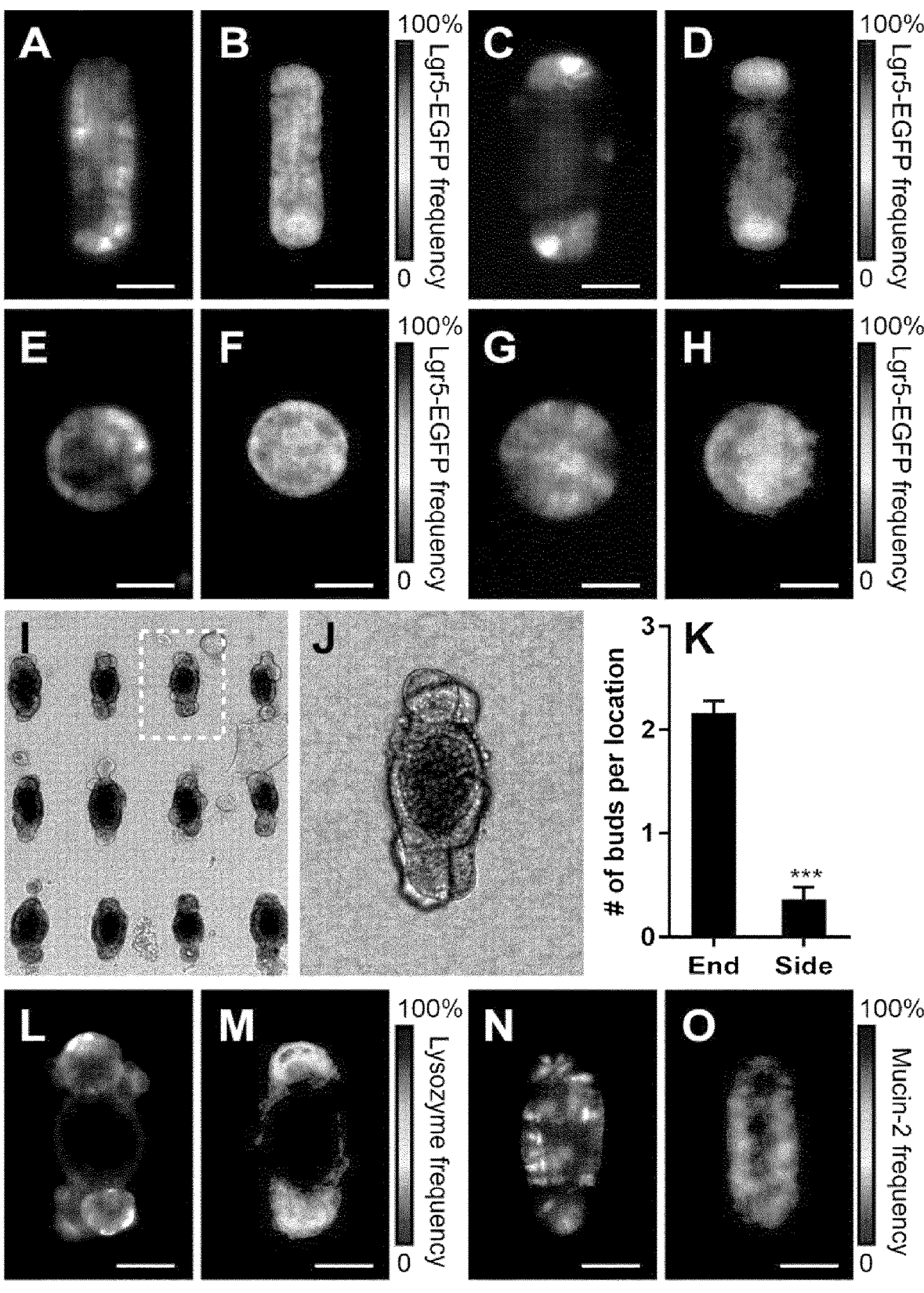

FIG. 2 Geometric control of intestinal tissue patterning (A) Lgr5-EGFP within a single tissue and (B) average distribution of Lgr5-EGFP within tubular intestinal tissues cultured under ISC expansion conditions. (C) Lgr5-EGFP within a single tissue and (D) average distribution of Lgr5-EGFP within tubular intestinal tissues cultured under organoid formation conditions. (E) Lgr5-EGFP within a single circular tissue and (F) average distribution of Lgr5-EGFP within circular intestinal tissues cultured under ISC expansion conditions. (G) Lgr5-EGFP within a single circular tissue and (H) average distribution of Lgr5-EGFP within circular intestinal tissues cultured under organoid formation conditions. (I) An array of intestinal organoids formed from engineered intestinal tissues of tubular geometry, and (J) magnification. (K) Quantification of the average number of buds per location within tubular intestinal tissues. Lysozyme-expressing Paneth cells within (L) a single tubular intestinal tissue and (M) average Paneth cell distribution within tubular intestinal tissues. Mucin-expressing goblet cells within (N) a single tubular intestinal tissue and (O) average goblet cell distribution within tubular intestinal tissues. Scale bars, 50 μm.

Figure 3:
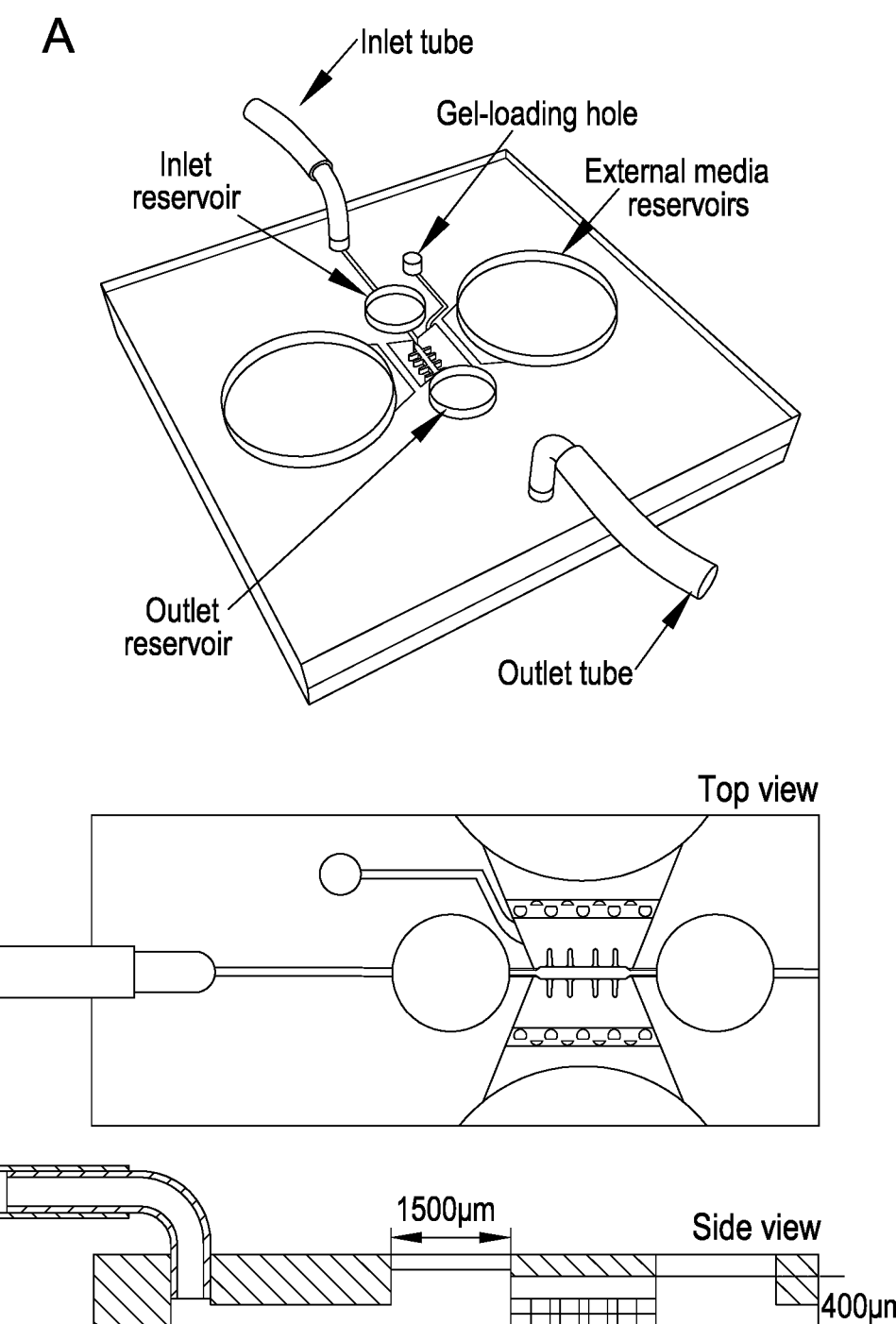
Figure 3:
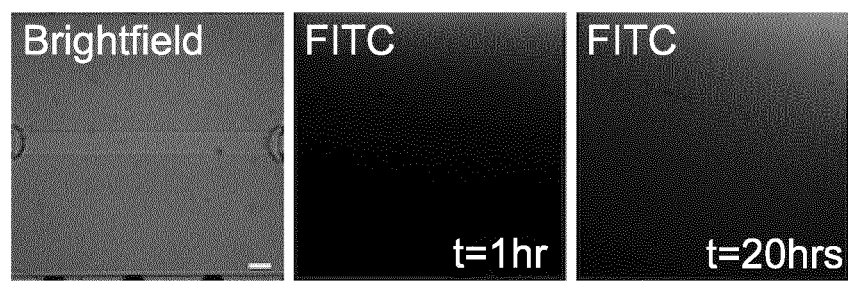
Figure 3:
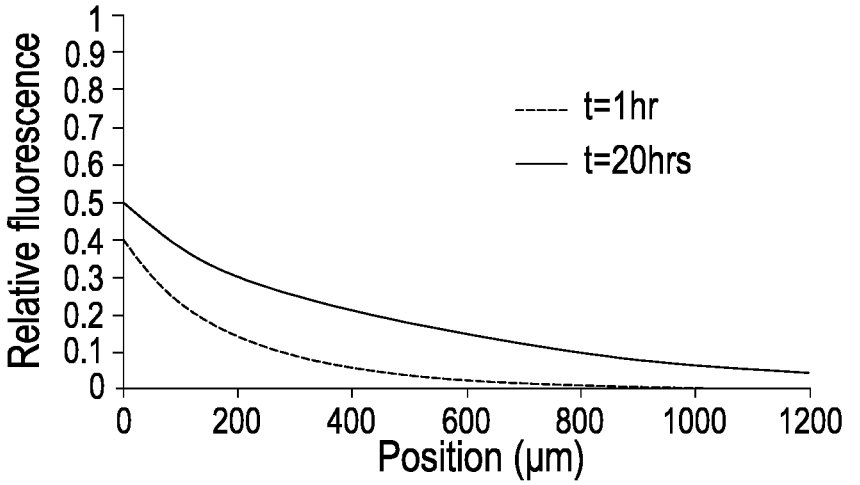
Figure 3:
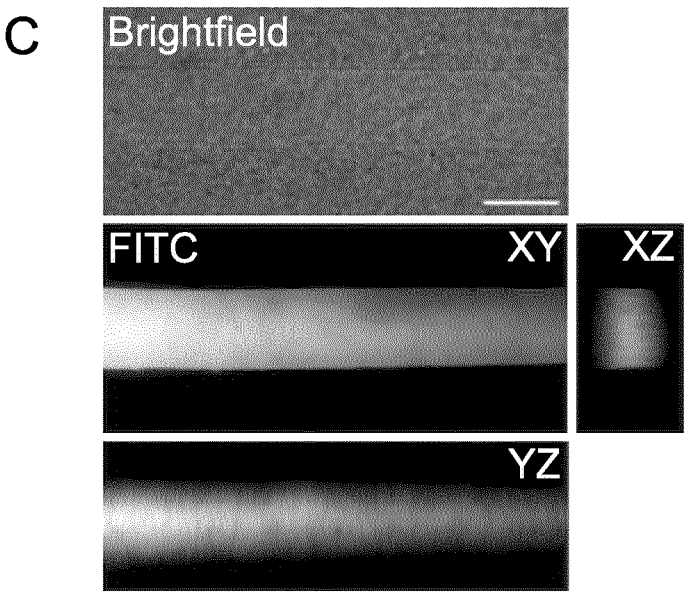

FIG. 3 Intestinal tube microdevices

This shows a 3D microdevice ("OrganoChip") for culture of organotypic intestinal tubes. (A) The microdevice consists of five compartments: a matrix chamber in the center, flanked by two external media reservoirs and two reservoirs (inlet and outlet) for media perfusion. The 3D microtrack covering the entire length of the matrix compartment is generated by laser ablation. Top right: detailed top view. Bottom right: detailed side view. (B) Media reservoirs are used as source of diffusive signals. Bright-field and fluorescence image of the matrix compartment with a laser ablated matrix microtrack, 1 and 20 hours after addition of 40 kDa FITC-Dextran to one of the reservoirs. Bottom: Quantification of the fluorescence profile across the matrix chamber (1200 μm) in relation to the source at 1 and 20 hours. Media in the reservoirs was not replenished. (C) Bright-field and confocal images of a laser ablated matrix microtrack filled with 2000 kDa FITC-Dextran. XY corresponds to maximal projection, XZ and YZ to orthogonal projections, of a 210 μm z-stack. Scale bar, 100 μm.

Figure 4:
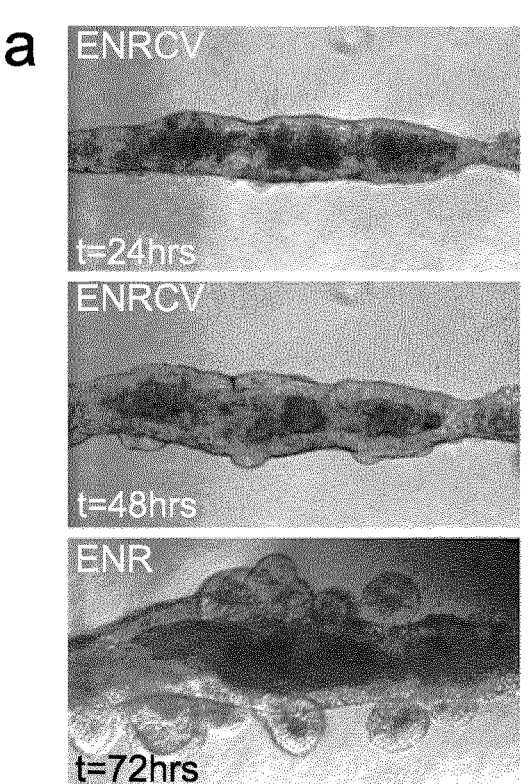
Figure 4:
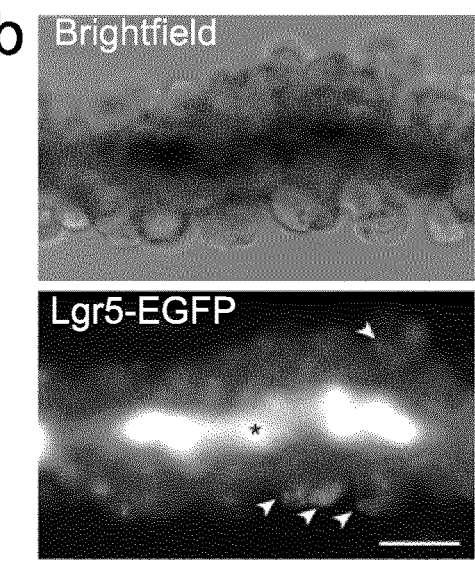
Figure 4:
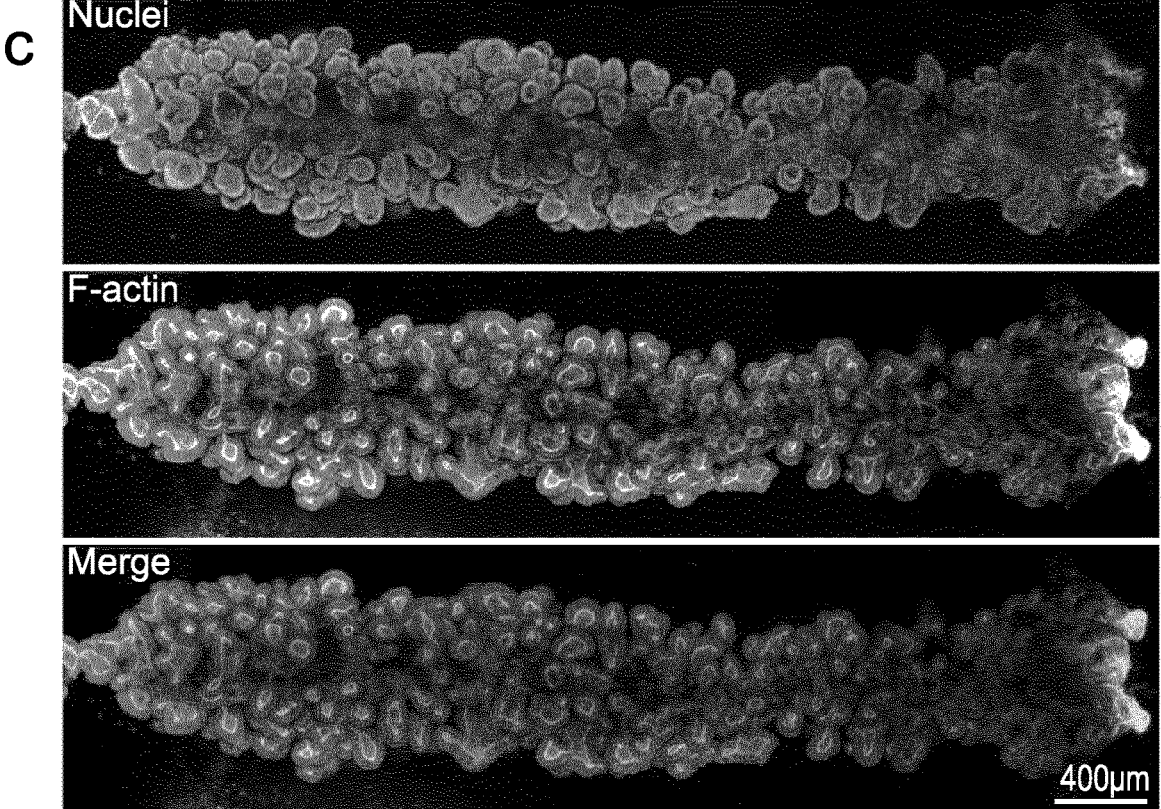
Figure 4:
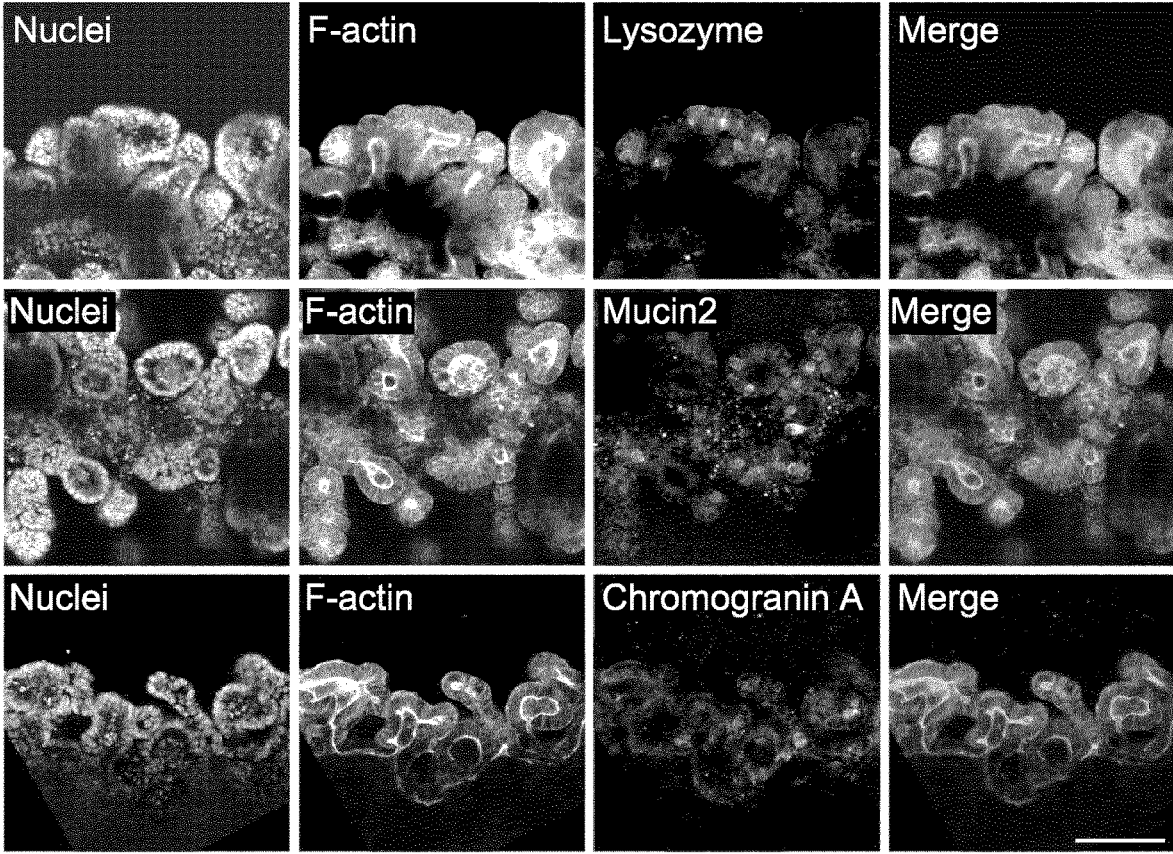

FIG. 4 Culturing ISCs as intestinal tubes (a-b) Visualization of ISCs grown in intestinal tubes: (b) bright field and (c) F-actin/nuclei staining. (d) Expression of lysozyme, mucin-2 and chromogranin A.

Figure 5:
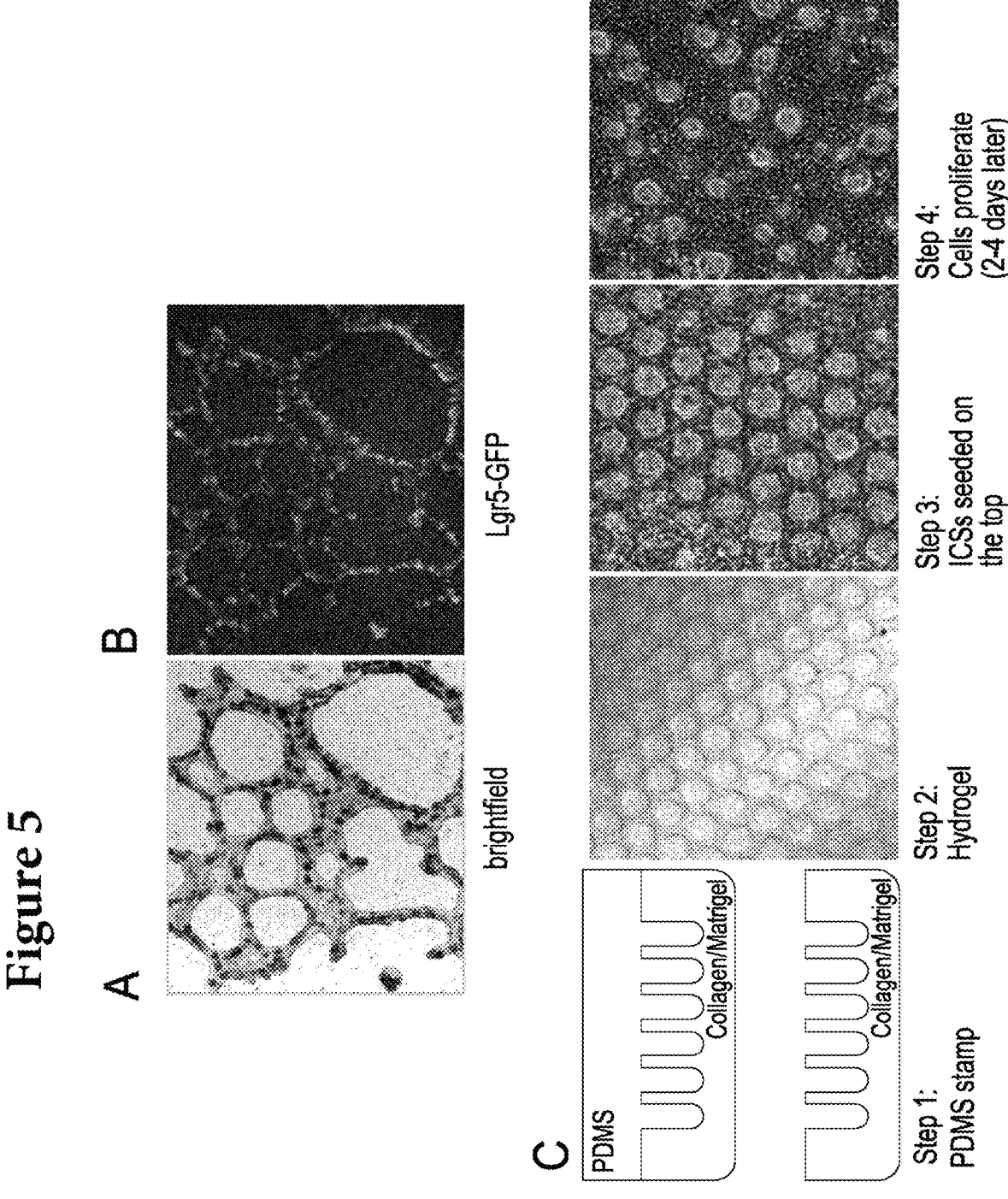
Figure 5:
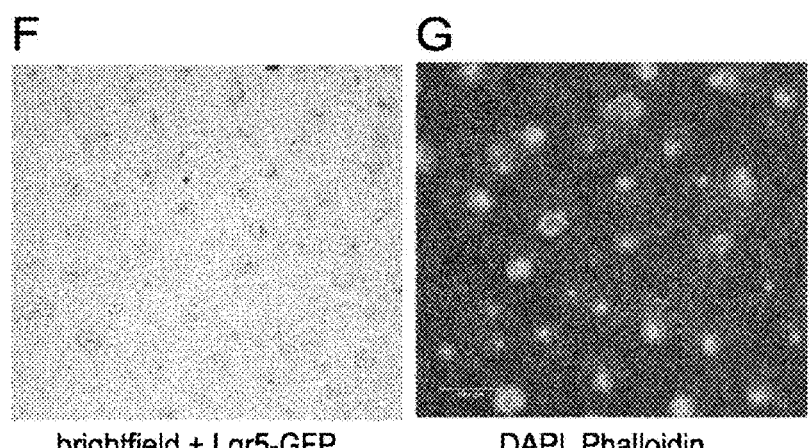
Figure 5:
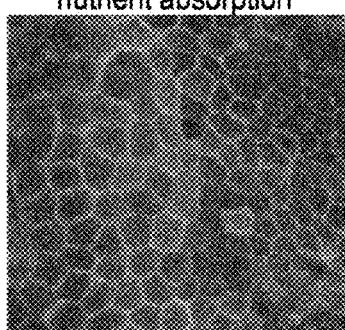
Figure 5:
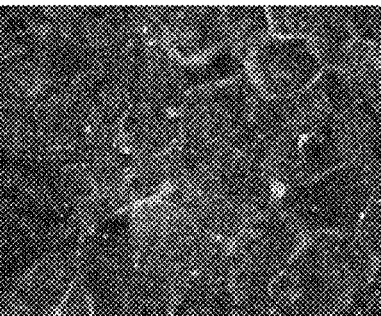
Figure 5:
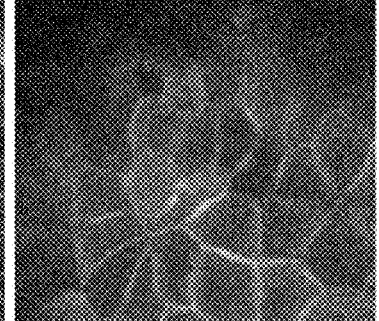
Figure 5:
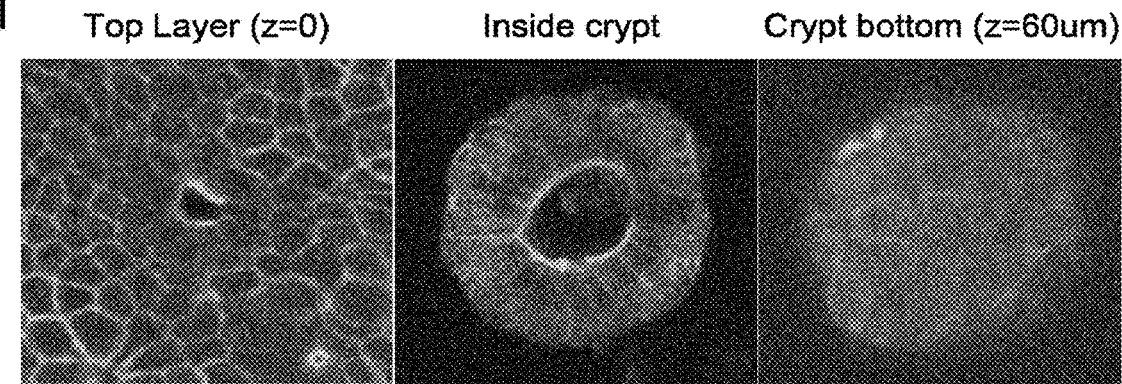
Figure 5:
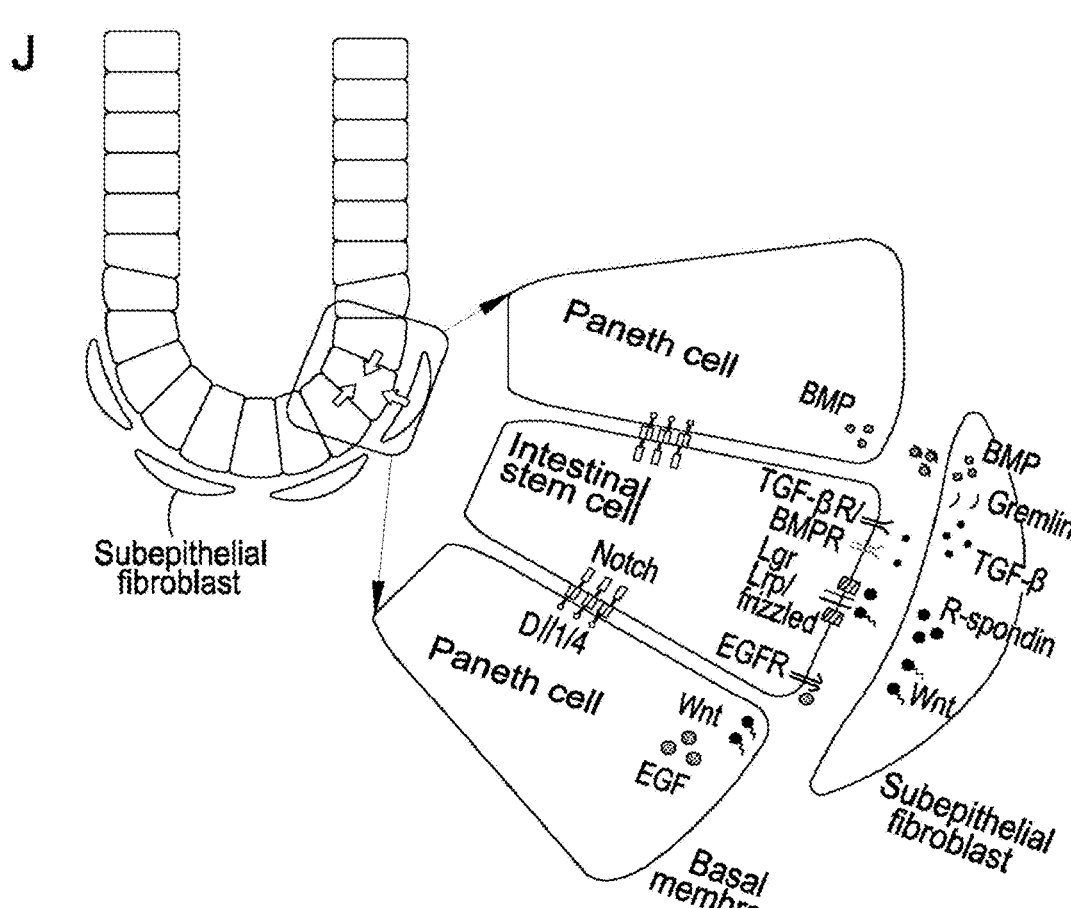
Figure 5:
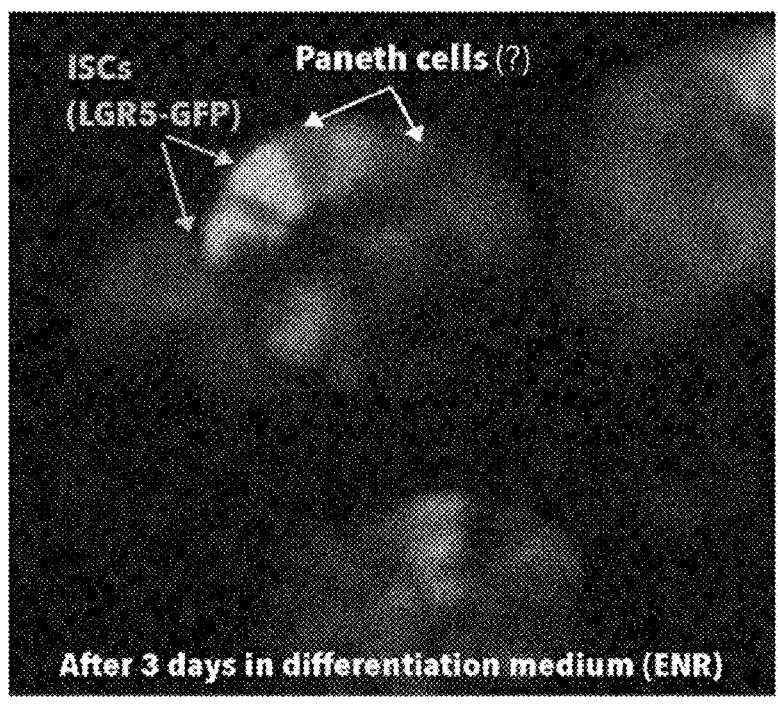
Figure 5:
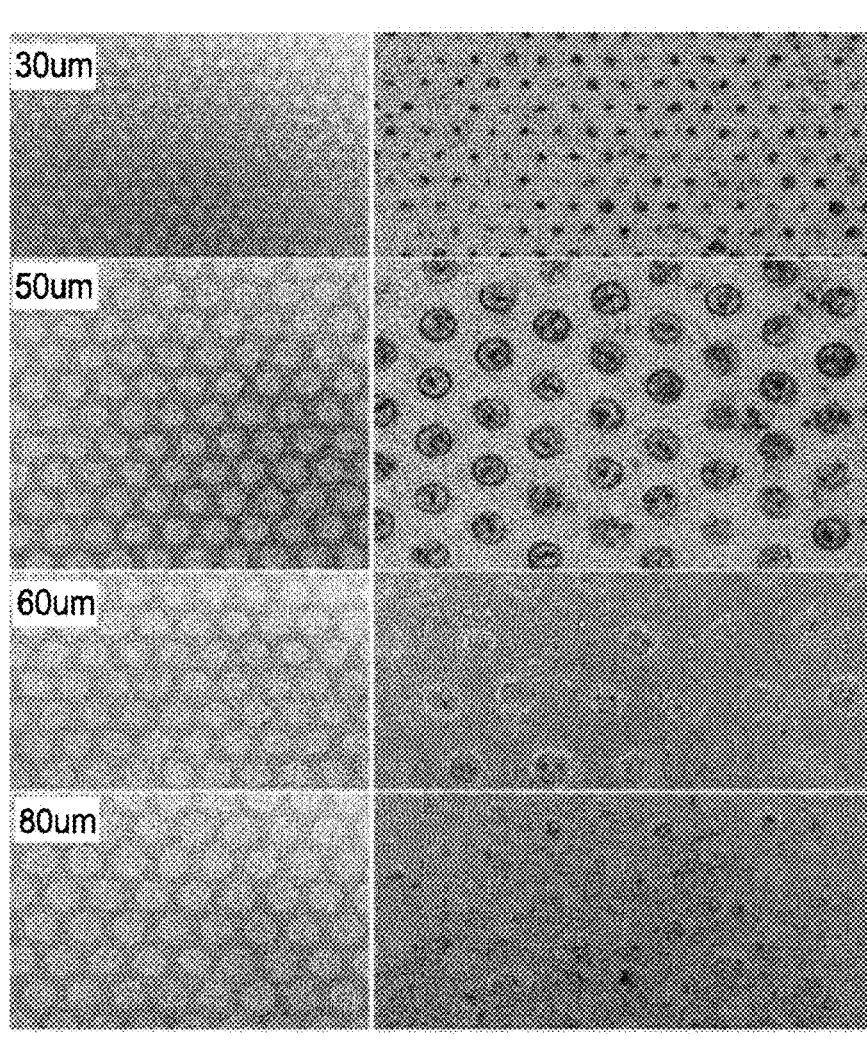

FIG. 5 Engineering of intestinal surfaces (A) Intestinal stem cells form continuous layers when seeding at high density onto a Matrigel surface, shown by bright field imaging and (B) LGR5-GFP expression. (C) This approach could be applied to form a continuous layer of cells on gels possessing intestine-like micro-topography. (D) Schematic of surface design. (E) Cross-section view of the replica from PDMS mould (scanning electron microscopy) (F, G) ISCs were maintained following culture of the cell layer in differentiation conditions, phalloidin=F-actin stain. (H) Cell types in grown intestinal epithelial layer. (I) Morphology of the fabricated crypts. (J) Localization of Paneth cells in the layers. (K) Diameter of microwells controls crypts formation. Bright-field images of the microwells in hydrogel (left column) and corresponding cell layer, 72 hours after seeding mISCs.

Figure 6:
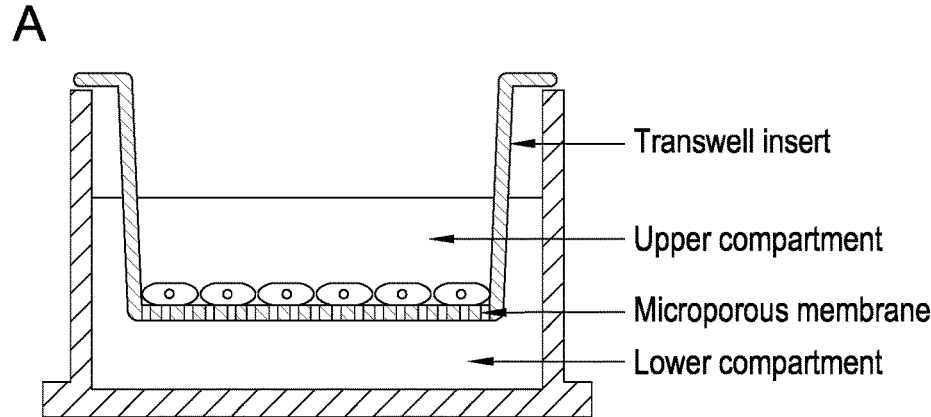
Figure 6:
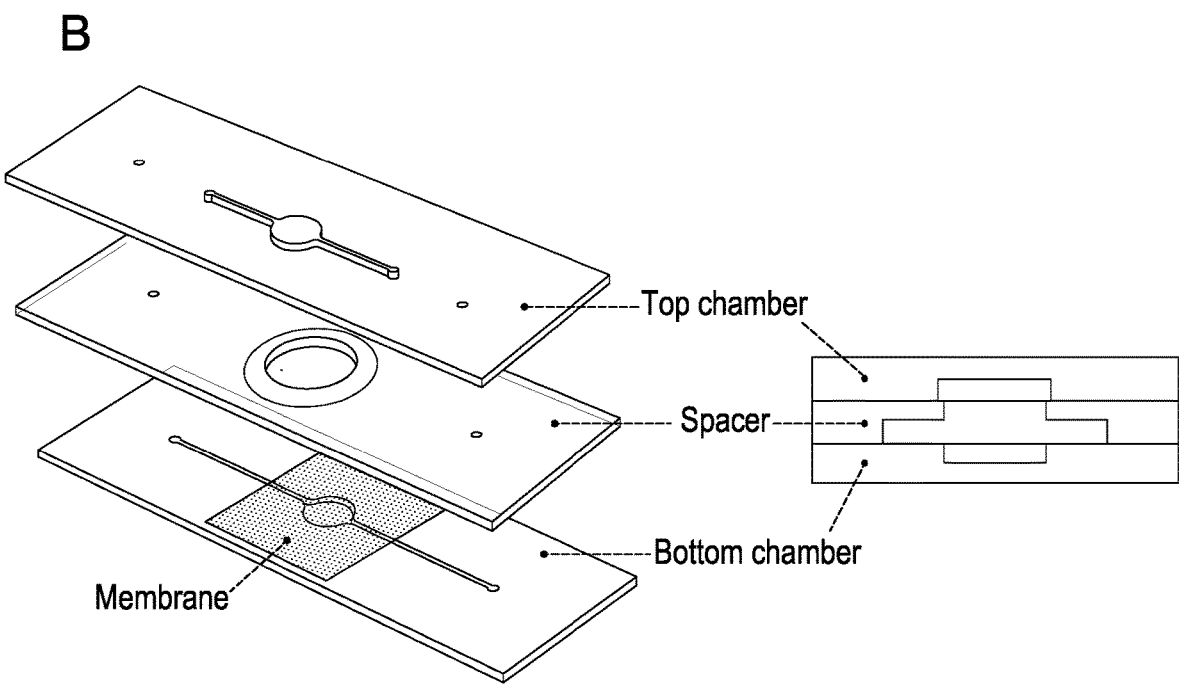

FIG. 6 Microfluidic chip design (A) Schematic of a standard transwell. (B) Schematic of the dynamic microfluidic chip design.

Figure 7:
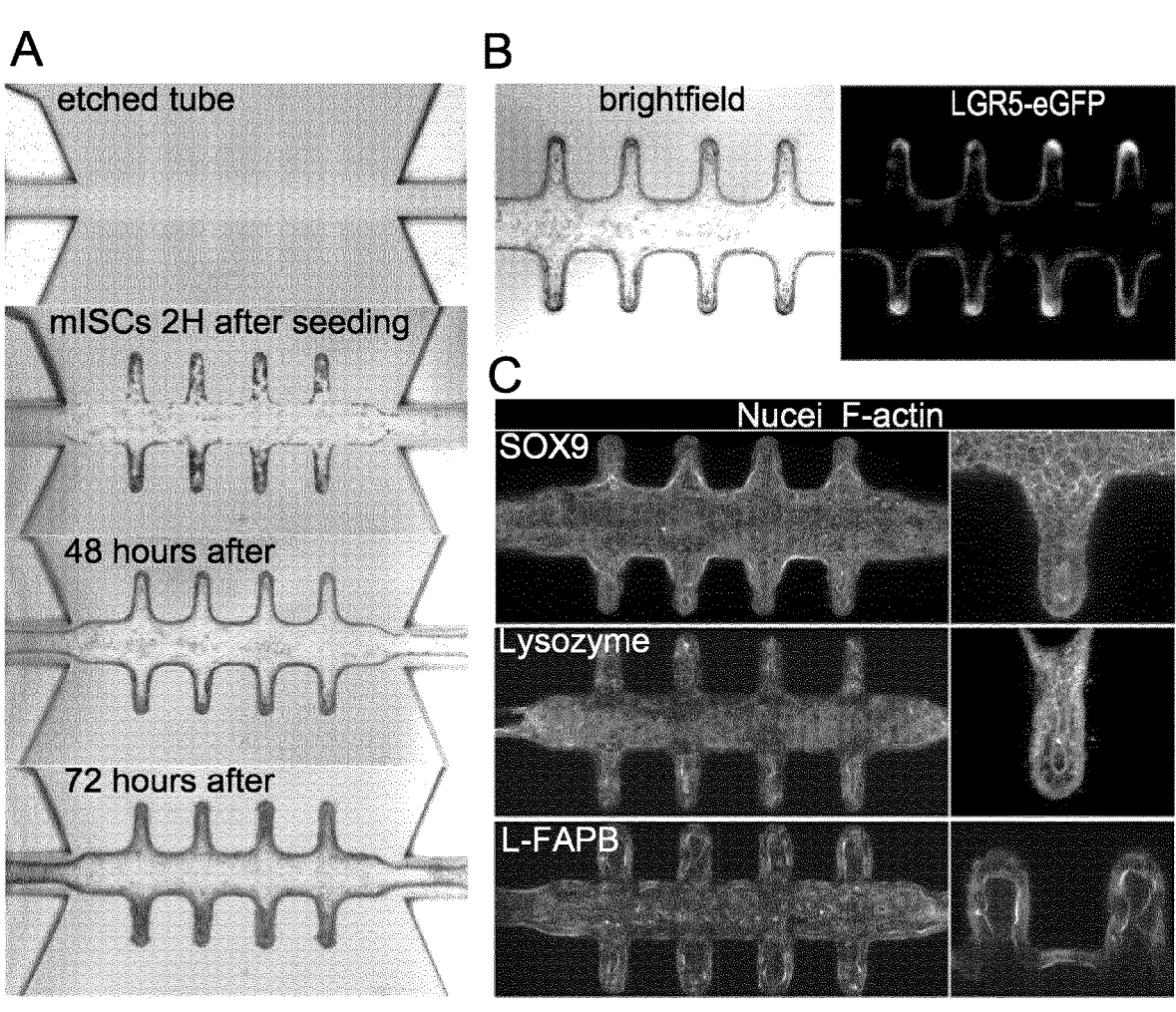

FIG. 7 Geometrically guided self-organization of mISCs into tubular organoids (A) Bright-field time course of mISCs cultured in the matrix microtrack of the OrganoChip microdevice. (B) Bright-field and fluorescence confocal images of the LGR5-eGFP mISCs grown for 5 days (2 days in self-renewal conditions+3 days in differentiation conditions). (C) Fluorescence confocal images of an intestinal tube grown for 5 days (2 days in self-renewal conditions+3 days in differentiation conditions) in the microdevice. Cells were labelled with DAPI for the nuclei (blue) and Phalloidin for F-actin (green) and sox9 (red, stem/progenitor cells), lysozyme (red, Paneth cells) and L-FABP (red, enterocytes). Images correspond to maximal projection of 80 μm z-stack.

Figure 8:
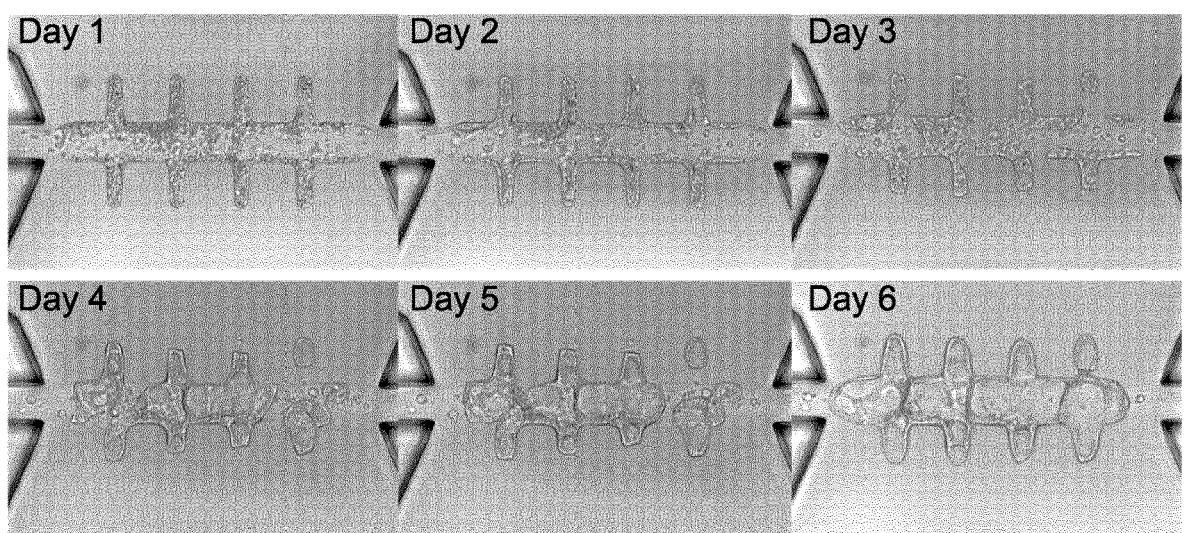

FIG. 8 Bright-field time course of human iPS cells cultured in the tube-shaped matrix microtrack of the "OrganoChip" microdevice.

DEFINITIONS

An array as used herein is defined as an ordered arrangement of similar or identical objects. Typically, the objects in an array can be divided into rows and columns. An array of organoids is an ordered arrangement of organoids. In biology, arrays of samples or biological materials (microarrays) are used for high-throughput analysis.

Cartigel is an extracellular matrix extract of cartilage.

Crosslinkable by cell-compatible reaction(s) comprise reactions on the basis of (i) permanent covalent bond formation, chosen from the group consisting of a) enzymatically catalyzed reactions, preferably depending on activated transglutaminase such as factor XIIIa; and b) not-enzymatically catalyzed and/or uncatalyzed reactions, preferably a Michael addition reaction; and/or ii) reversible covalent bond formation, chosen from the group consisting of Schiff base (imine) bonds, reversible hydrazone bonds, oxime bonds, disulfide bonds and bonds formed by reversible Diels-Alder reactions; and/or iii) non-covalent (i.e. physical) bond formation (e.g. on the basis of hydrophobic interactions, H-bonds, van-der-Waals, electrostatic interactions, host-guest interactions, biorecognition (domain/protein-ligand interactions); spontaneous or induced by temperature changes or changes in ionic strength of a buffer).

A focal plane is the plane or flat surface through the focus perpendicular to the axis of a lens of, for example, of a microscope. At a particular focus, all objects in view are within the same focal plane.

A biofunctional hydrogel is a hydrogel that contains bioactive (or bio-adhesive) molecules, and/or cell signaling molecules that interact with living cells to promote cell viability and a desired cellular phenotype. Biofunctional hydrogels may also be referred to as bioactive. Examples of bio-adhesive molecules include, but are not limited to, fibronectin, vitronectin, bone sialoprotein, laminin, collagen and elastin. These molecules contain cell adhesive peptides that govern their interaction with cells. Examples of cell adhesion peptide sequences include, but are not limited to, fibronectin-derived RGD, KQAGDV, REDV and PHSRN, laminin-derived YIGSR, LGTIPG, IKVAV, PDGSR, LRE, LRGDN and IKLLI, collagen-derived DGEA and GFO-GER, and elastin-derived VAPG. A dilute hydrogel or 3D matrix is a hydrogel that does not polymerize, a non-dilute hydrogel or 3D matrix forms a gel.

Bio-active (or bio-adhesive or biofunctional) molecules are molecules that interact with cells to promote cell viability and have been previously described for a variety of cell types. Bio-adhesive molecules that render a hydrogel bio-functional include, but are not limited to, fibronectin or functional variants thereof, for example FF III1-C fragment, FNIII9-10 fragment, and FNIII12-14, or RGD containing peptides, for example RGD, RGDS, RGDSP, RGDSPK, RGDTP and RGDSPASSKP. Functional variants of bioactive molecules are molecules having the same or similar biological or biochemical function and a similar sequence or composition—for example, truncated molecules, or fragments of such molecules.

A biocompatible hydrogel is a polymer network that is not significantly toxic to living tissue and/or cells, and does not elicit an immunopathogenic response in healthy individuals. A biocompatible active mechanism is a process that is not toxic to particular cells or tissues, for example a temperature increase within the physiological temperature range of tissues, or that is applied briefly enough so as not to cause significant toxicity.

A cavity is an indent, well, inverse 3D structure or partly enclosed space. A cavity can be of any shape or size. A mould harbouring the inverse of the cavity has the 3D structure of the space enclosed by the cavity, and/or the inverse of the external surface of the cavity.

A colony is a population of two or more conspecific cells living in close association with, or connected to, one another.

Culturing cells refers to the process of keeping cells in conditions appropriate for maintenance and/or growth, where conditions refers to, for example, the temperature, nutrient availability, atmospheric $CO_2$ content and cell density in which the cells are kept. Cells can be cultured in vivo or in vitro. The appropriate culturing conditions for maintaining, proliferating, expanding and differentiating different types of cells are well-known and documented. The conditions suitable for organoid formation are those that facilitate or permit cell differentiation and the formation of multicellular structures. See Materials and Methods for details of culturing conditions suitable for the cells used in the examples.

High-throughput screens and assays are those which are automated to achieve levels of repeatable data acquisition unfeasible using manual methods.

A hydrogel (gel) is a 3D matrix comprising a network of hydrophilic polymer chains.

In situ is a biological term for culturing cells or tissues without moving their position, that is, to maintain them in their natural place or position.

Laminins are a family of extracellular matrix glycoproteins that have a heterotrimeric structure consisting of an α, β and γ chain. Laminin-111 is synonymous with Laminin-1. Laiminin-111 is encoded by the LAMA1 gene.

Matrigel is a commercial product widely used in both 2D and 3D models of cell culture. It comprises a solubilized basement membrane preparation extracted from an ECM rich mouse tumour.

A microwell is a cavity capable of holding liquid, comprising an open mouth, a hollow shaft and a bottom. A microwell can also be referred to as a well, microcavity or cavity. Microwell plates comprise arrays of equivalent microwells. These microwells may form patterns in the substrate forming the plate, for example to form a patterned hydrogel. Microwells may be flat-bottomed, round (U)-bottomed, V-bottomed or conical flat bottomed. The shaft of a microwell is typically cylindrical. The depth of a microwell refers to the distance from the mouth to the lowest part of the bottom. Microwells may have any shape, including round, oval, rod-like, rectangular, etc.

Myogels are extracellular matrices extracted from skeletal muscle (Abberton et al., 2008).

Organoids are three-dimensional culture systems of organ-specific cell types that develop from stem cells or tumour cells and self-organize (or self-pattern) through cell sorting and spatially restricted lineage commitment in a manner similar to the situation in vivo. As used herein, an organoid is defined as a 3D culture of stem cells or tumour cells and their differentiated progeny, initiated from a single stem cell or a multicellular aggregate of cells with at least one stem cell. Stem cells may be isolated from tissue or organoid fragments. Organoids grown from isolated intestinal crypts or stem cells may also be referred to in the field as "enteroids" or "colonoids". Organoids grown from or containing cancerous cells are "tumoroids".

An organ-on-a-chip is a microfluidic cell culture device that contains continuously perfused chambers inhabited by living cells arranged to simulate tissue- and organ-level physiology (Bhatia and Ingber, 2014).

Predetermined is used herein to describe results that are predictable and reproducible. An organoid with a predetermined cellular shape and patterning has a cellular shape and patterning that can be reliably and repeatedly produced by a known method, i.e. the organoid's shape and patterning is determined by choosing this repeatable method to produce it.

The term RGD or RGD sequence refers to a minimal bioactive RGD sequence, which is Arginine-Glycine-Aspartic Acid (RGD) sequence, and which is the smallest (minimal) fibronectin-derived amino acid sequence that is sufficient to mimic cell binding to fibronectin and/or to promote adhesion of the anchorage-dependent cells.

Seeding cells refers to the process of allowing a suspension of cells to settle onto a surface through gravity or centrifugation.

The tissue shape and patterning of an organoid may be defined in terms of the type and/or relative positions of the cells and tissues forming the organoid structure. The tissue shape and patterning of an organoid can also be defined in terms of the number, type and/or relative positions of substructures, such as lumen, within the organoid. Tissue shape and patterning includes, for example, the presence and location of morphogenetic structures or buds within the 3D epithelial tissue and the results of spatial patterns of differentiation.

The shear modulus of a hydrogel is equivalent to the modulus of rigidity, G, elastic modulus or elasticity of a hydrogel. The shear modulus is defined as the ratio of shear stress to the shear strain. The shear modulus of a hydrogel can be measured using a rheometer (Example 1, 1.4 Materials and Methods).

Surface is used herein describe a structure or substrate on or in which cells can grow. The surface may be patterned, for example with cavities or microwells.

A torus tubular shape is formed by rotating a closed curve about a line which lies in the same plane but does not intersect it. R is the distance from the center of the tube to the center of the torus, r is the radius of the tube. The ratio R divided by r is known as the aspect ratio.

A tube is a hollow cavity with a longitudinal axis that may have a circular, elliptical and/or rectangular cross-section. In contrast to a cavity, a tube has two open ends that allow perfusion with liquid, i.e. a tube is perfusable cavity.

DESCRIPTION

A method for obtaining an organoid having a pre-determined tissue shape and patterning, comprising:

i. seeding one or more self-renewing cells capable of differentiating to form an organoid onto a surface having a 3D structure, ii. culturing the seeded cells under self-renewal conditions such that the cells proliferate and pattern to form a colony having the same 3D structure as the surface, and iii. culturing the colony under differentiation conditions such that the colony undergoes morphogenesis to form an organoid.

Organoid formation of step iii may include the colony undergoing changes in cell fate that are spatially patterned by the initial geometry (that is, the initial geometry of the colony, which in turn is defined by the 3D structure of the surface), and subsequent morphogenesis to form an organoid. The organoid has reproducible and predictable morphological features (for example, crypts and/or buds).

In one embodiment the self-renewing cells are stem cells or tumour cells, preferably embryonic, induced pluripotent, small intestinal, stomach, colon, pancreatic, liver, lung, prostate, mammary, corneal, hair follicle, epidermal or kidney stem cells or progenitors of such cells.

In another embodiment the 3D structure may be of any desired shape or size, preferably wherein the structures are fabricated on the surface and/or within the surface, wherein the surface may be a macroscopic block of hydrogel.

Preferably, the 3D structure on the surface may comprise microwells, micropillars, or a combination of both, preferably wherein the surface is a hydrogel. More preferably, the 3D structure has minimum thickness that is equivalent to at least 3 layers of the self-renewing cells or other cell type, and is maximally limited by the size of the surface 3D hydrogel. More preferably, the structure may comprise cavities that are arranged in array.

The 3D structure may also be formed from cavities within the surface, preferably wherein the surface is a macroscopic block of hydrogel. Preferably, the cavity is a tube, more preferably wherein the tube is open and perfusable.

The cavity may be tubular in shape, wherein the tube has a rectangular cross section, preferably wherein the rectangle has sides that are between 10 μm and 5 mm in length. The tube may alternatively or additionally have an elliptical cross-section, preferably wherein the ellipse has two principal axes between 10 μm and 5 mm in length, more preferably wherein one principal axis is longer than the other principle axis. The tube may have a rectangular cross section through one section of its longitudinal axis and an elliptical cross-section through another section or sections of its longitudinal axis.

The cavity may also or alternatively have a 3D structure comprising a cylinder, preferably wherein the cylinder has a diameter of 10 μm to 5 mm, more preferably wherein the cylinder has a total length between 10 μm to 50 mm.

The cavity may have a 3D structure comprising a torus, preferably wherein the torus has an R value of between 100 μm and 5 mm, more preferably wherein the torus has an r value of between 10 μm and 1 mm.

In another embodiment, the method of the invention the pre-determined 3D structure is obtained by replica moulding, soft embossing, injection moulding, 3D printing, bioprinting, laser machining, micromachining, surface etching, optical lithography, additive manufacturing, electrochemical directed crosslinking soft-lithography, and/or polydimethyl siloxane (PDMS) replica moulding.

The substrate of the invention may be a hydrogel. The hydrogel of the invention may be formed of macromolecules of natural origin and selected from the group comprising polysaccharides, gelatinous proteins, agarose, alginate, chitosan, dextran, laminins, collagens, hyaluronan, fibrin or mixtures thereof, or are selected from the group of complex tissue-derived matrices consisting of Matrigel, Myogel and Cartigel.

Preferably the hydrogel comprises a mix of type I collagen and Matrigel, preferably wherein the concentration of collagen in the gel is between 0.4 mg/ml and about 3.6 mg/ml, more preferably wherein the Matrigel is at a percentage between 90% (v/v) and 10% (v/v). Alternatively the hydrogel may be formed of macromolecules that are synthetic or recombinant, preferably crosslinked synthetic hydrophilic polymers functionalized with an extracellular matrix (ECM)-derived protein or peptide, preferably wherein the hydrophilic polymer is selected from the group comprising: poly(ethylene glycol), polyoxazoline, polyaliphatic polyurethanes, polyether polyurethanes, polyester polyurethanes, polyethylene copolymers, polyamides, polyvinyl alcohols, poly(ethylene oxide), polypropylene oxide, polypropylene glycol, polytetramethylene oxide, polyvinyl pyrrolidone, polyacrylamide, poly(hydroxy ethyl acrylate), poly(hydroxyethyl methacrylate) and mixtures or co-polymers thereof. The hydrogel may also be a mix of Matrigel and a synthetic gel.

In an embodiment, the hydrogels used, which are obtained by cross-linking hydrogel precursor molecules, are preferably composed of hydrophilic polymers such as poly(ethylene glycol) (PEG)-based polymers, most preferably multiarm (i.e. branched) PEG-based polymers that are crosslinked by cell-compatible crosslinking reactions. Hydrogel precursors can be selected from a group comprising linear PEG molecules, or multiarm PEG hydrogel precursor molecules, preferably those bearing 4- or 8-arms. Hydrogel precursors can be further selected from a group comprising PEG hydrogel precursor molecules with molecular weight of 10-40 kDa.

In another embodiment of the invention the ECM-derived protein or peptide is selected from the group comprising laminin-111, laminin-511, laminin-521, laminin-421, laminin-411, laminin-332, laminin-221, laminin-211, fibronectin, vitronectin, collagen I, collagen IV, perlecan, tenascin, hyaluronic acid, RGD, RGDS, RGDSP, RGDSPK, RGDTP, RGDSPASSKP, Cyclo(RGDSP), Cyclo(RGDFK), Cyclo (RGDYK), Cyclo(RGDFC), the III1-C fragment, FNIII9-10 fragment, and FNIII12-14 fragment, IKVAV, YIGSR and AG73.

In another embodiment, the hydrogel may be heterogeneous and comprise areas of locally different physicochemical properties and composition. Preferably, such hydrogels can include areas of different chemical composition or different physical properties on the surface as well as inside the gel.

In another embodiment of the invention, different types of support cells can be cultured inside the hydrogel. Preferably, these cells are mesenchymal-type cells, more preferably selected from the group comprising fibroblasts, myoblasts, myofibroblasts and adipocytes. Alternatively, endothelial cells and immune cells such as lymphocytes, B cells, macrophages and dendritic cells can be co-cultured in the hydrogel.

The stem cells may be pluripotent stem cells or somatic stem cells, preferably small intestinal, stomach, colon, pancreatic, liver, lung, prostate, mammary, corneal, hair follicle, epidermal or kidney stem cells, or progenitors of such cells, derived from tissues biopsies and/or expanded in vitro. More preferably, the stem cells are intestinal stem cells, such that the tissue-like colony comprises an epithelial-like tissue, more preferably wherein the epithelial-like tissue comprises a lumenized multicellular structure.

In another aspect the invention relates to an organoid produced by any of the methods of the invention. The organoid may be a tumouroid.

In yet another aspect the invention relates to an organoid having a pre-determined 3D shape/geometry, wherein the organoid is derived from a tissue-like colony formed in situ from a population of stem cells and the pre-determined cellular shape and patterning is determined by the 3D structure of the population of stem cells.

In one embodiment the organoid is an epithelial organoid and the pre-determined cellular shape and patterning comprises a cystic structure, a central lumen and an external layer of cells comprising a bud emerging at a region of high convex curvature within the initial structure.

In another aspect the invention relates to an array of the organoids within a 2D plane, preferably wherein the organoids are equally spaced within the array, preferably wherein the space between adjacent organoids in the array is equal to or greater than the length of any of the adjacent organoids within the plane of the array.

The size of the array may be between 10 μm to 100 mm in width and/or length. The may be folded to form a 3D shape, preferably a tube. The cavities of the array may be of any shape, but are preferably tubular and/or rectangular.

In another aspect the invention relates to the use of any of the methods of the invention to screen pharmacologic compounds, biomolecules or cells for their effect on organoid formation, the use comprising seeding cells in the presence of the pharmacologic compounds, biomolecules or cells to be tested, and monitoring the effect of the pharmacologic compounds, biomolecules or cells on organoid formation.

In another aspect the invention relates to the use of the organoids of the invention to screen pharmacologic compounds, biomolecules or cells for their effect in treating epithelial tissue diseases, wherein the organoid is an epithelial cell organoid or epithelial tumour cell organoid, preferably wherein the stem cells are, or are derived from stem cells that are, isolated from a tissue biopsy sample, the use comprising culturing the organoids in the presence of the pharmacologic compounds or biomolecules to be tested, and monitoring the reduction in cell and stem cell damage or death, restoration of epithelial junction integrity, inflammation and/or transepithelial transport. The epithelial tissue diseases may be a genetic, acquired, multifactorial, malignant or infectious disease, preferably wherein the disease is selected from the group comprising: cystic fibrosis, tufting enteropathy, ulcerative colitis and Crohn's disease. In one embodiment the use may be applied to an array of organoids, preferably wherein the use is performed in high-throughput.

The present invention also relates to the use of an organoid as described herein (preferably for example engineered intestinal tubes) as a means to model intestinal epithelial damage and regeneration. Perfusion with dextrane sulfate sodium (DSS) or exposure to radiation have been routinely used to model inflammation and damage in the native murine intestine, and study the subsequent regenerative process in vivo (Chassaing et al, Curr Protoc Immunol 2014; Metcalfe et al, Cell Stem Cell 2014). Although the field would greatly benefit from in vitro models of damage and repair in the human intestine, classical organoid models are not suitable for this purpose, as their small size and closed, inside-out structure makes them overly sensitive to DSS- and radiation-induced damage, leading to full destruction and failure to regenerate. The method described herein may comprise:

1. Creating an engineered intestinal tube using biopsy- or iPSC-derived human ISCs.
2. Perfusing with DSS or exposure to radiation to induce intestinal epithelial damage.
3. Monitoring and studying endogenous wound healing and epithelial repair processes.
4. Screening pharmacologic compounds that support and enhance regeneration and repair.

In addition to developing methods for producing clinical-grade ISCs and organoids, a major hurdle in using organoids in cell-based therapies in humans is the optimization of delivery and grafting strategies. We propose that engineered epithelial tubes as described here can be used to model organoid-based approaches to treat epithelial damage. The method may comprise:

1. Creating an engineered intestinal tube using biopsy- or iPSC-derived human ISCs.
2. Perfusing with DSS or exposure to radiation to induce intestinal epithelial damage.
3. Introducing ISCs or intestinal organoids to optimize delivery and grafting in the context of cell-based therapy of intestinal damage or disease.

In another aspect the invention relates to a kit for making 3D structures suitable for the method of invention, comprising i) a mould harbouring the inverse of the 3D cavities, and ii) a hydrogel of the method of the invention. The kit may also comprise stem cells.

In another aspect the invention relates to a kit for making an organoid-based organ-on-a-chip system comprising i) a microdevice surface comprising the 3D structure of any of the methods of the invention, ii) medium providing self-renewal conditions and/or differentiation conditions suitable for culturing stem cells iii) stem cells, preferably epithelial stem cells.

In one embodiment the colony is structurally similar to an epithelial tissue (i.e. epithelial tissue-like).

In one aspect the invention relates to an epithelial stem cell organoid which comprises a cystic structure, a central lumen, and on the outside a layer of cells with at least one bud emerging at regions of high convex curvature within the initial structure.

In another aspect the invention relates to the use of an array of organoids for quantifying epithelial stem cell or tumour cell organoid formation, the method comprising:

1. seeding a plurality of self-organizing epithelial stem or tumour cells onto arrays of organoids according to the invention,
2. culturing said cells under suitable conditions in the presence of pharmacologic compounds, biomolecules, or cells, and
3. monitoring, by quantitative, high-content imaging approaches, the self-organization of said cells into organoids.

In another embodiment the invention relates to the use of an array of organoids of the invention for screening of candidates or libraries of pharmacologic compounds, biomolecules or evaluating cell-based therapies for efficacy in treating epithelial tissue diseases, the method comprising:

1. providing a tissue biopsy sample from a patient,
2. growing epithelial stem cells isolated from the biopsy sample in the array of organoids of the invention and culturing the arrayed organoids under suitable conditions in the presence of the pharmacologic compounds or biomolecules to be tested, and
3. monitoring the successful reduction in cell and stem cell damage or death, restoration of epithelial junction integrity, inflammation and transepithelial transport.

In certain embodiments the epithelial tissue disease is a congenital genetic disorder, for example, cystic fibrosis, tufting enteropathy, or an acquired or multifactorial disorder, for example, ulcerative colitis or Crohn's disease.

In another aspect the invention relates to the use of an array of organoids of the invention for screening of libraries of pharmacologic compounds, biomolecules or evaluating cell-based therapies for their efficacy in inducing epithelial tumour cell death or growth arrest, the method comprising:

1. growing tumour organoids in the array of the invention and culturing them under suitable conditions in the presence of the pharmacologic compounds, biomolecules or cells to be tested, and
2. monitoring cell death and/or growth arrest.

Epithelial tumours include epithelial ovarian cancer (Ramalingam, 2016), thyroid epithelial tumours (Eszlinger et al., 2008), renal epithelial tumours (Hagenkord et al., 2011), pancreatic tumours including solid and papillary epithelial pancreatic tumours (Madan et al., 2004) and epithelial neoplasms and carcinomas of any tissue type.

In yet another aspect the invention relates to the use of an array of organoids of the invention for quantifying the interaction between the microbiome and/or pathogens and epithelial stem cells and their differentiated progeny, the method comprising:

1. seeding one or a plurality of self-organizing epithelial stem cells to form arrays of organoids of the invention, wherein the organoid comprises and accessible epithelium,
2. culturing said cells under suitable conditions in the presence of pharmacologic compounds, biomolecules, or cells, and
3. seeding a plurality of mixes of microbes onto said the accessible epithelium,
4. monitoring, by quantitative, high-content imaging, and trans-epithelium transport measurement approaches, the epithelium modifications and the interaction between the microbial population and the said epithelium.

Epithelial tissue diseases related to or associated with the interaction of the microbiome and/or pathogens with the epithelial tissue include ulcerative colitis, Crohn's disease, diarrhea, inflammatory colitis, necrotizing enterocolitis, hyperplasia, inflammatory bowel disease and microerosions.

In another aspect the invention relates to a kit of parts for making a hydrogel according to the invention, comprising the following components:

1. a mould harboring the inverse of the 3D cavities of the invention,
2. precursor or precursors of a substrate suitable for forming the surface of the invention, wherein the precursors include the components that are tethered to the substrate after formation.

In one embodiment the kit may comprise a mould contained within a culture container, preferably within a well or wells of a multiwell plate, a tube or tubes containing the precursor or precursors and a separate container comprising the mould. The parts of the kit are preferably provided pre-supplied in a container, preferably mounted on a moulding support. The precursor or precursors are preferably supplied in a substantially unreacted form, preferably in dried or dehydrated form.

In another aspect the invention relates to a kit of parts for making a stem cell derived organoid of pre-determined 3D shape, comprising spatially pre-defined 3D cavities on or within the substrate or surface, wherein the kit comprises the following components:

1. a defined pattern of 3D cavities according to the invention, imprinted on a substrate or surface;
2. the substrate or surface
3. a medium comprising tissue specific factors, nutrients and morphogens; and
4. stem cells.

The substrate may be prepatterned with the cavities and provided in a culture container. The media components may be provided in a separate vessel, preferably a tube or a bottle. The stem cells may be provided in yet another separate vessel, preferably a tube, preferably a cryotube.

Alternatively, components to form the substrate may be provided pre-supplied in a container, preferably in wells of a multi-well plate in a pre-reacted form, preferably immersed in liquid.

The media may be provided in a more than one ready-to-mix bottles and tubes, preferably more than two, more preferably more than three and preferably at low temperature.

The stem cells may be provided in a cryotube, preferably at very low temperatures.

The stem cells may be of epithelial origin, including, but not limited to gastrointestinal, mammary, liver, prostate, corneal, pancreatic, and of embryonic and induced pluripotent origin.

Self-renewal conditions according to the invention may comprise factors previously described to be necessary for culturing stem cell colonies of different origins in contact with an extracellular matrix, such as a BMP inhibitor, a Wnt agonist and Epidermal Growth Factor, added to a basal medium for animal or human cells culture.

Differentiation conditions according to the invention may comprise factors previously described to be necessary for culturing and obtaining stem cell organoids of different origins in contact with an extracellular matrix, not comprising either a BMP inhibitor or a Wnt agonist, added to a basal medium for animal or human cells culture.

In another aspect the invention relates to a microdevice that is manufactured via soft-lithography technique and polydimethyl siloxane (PDMS) replica moulding. The microdevice may be composed of multiple modules: one or multiple hydrogel compartments connected a inlet/outlet pair for cell loading are flanked by open medium reservoirs and air flushing channels. Compartments are partially delimited by obstructive features that guide the phase upon hydrogel loading, while interconnection allows for free exchange of dissolved molecules. Culture medium is stored in the open reservoirs and diverse media composition allows for generation of gradual spatial distribution of biomolecules. Air flushing channels allow for withdrawing residual air after complete polymerization of the hydrogel. Cells are injected to the cavity through the loading inlets.

The invention also relates to the use of such a microdevice for developmental and physiological studies, including interactions of stem cells and their differentiated progeny with the mesenchyme, as well as physiologically relevant synergistic interactions of stem cells and their differentiated progeny with cells of different species, such as bacteria. The microdevice could alternatively be used in epithelial tissue diseases studies, including, but not limited to studies of epithelial genetic, absorptive, infectious and malignant diseases. The microdevice could also be used in drug discovery screens, drug metabolism studies and toxicity assays.

In another aspect the invention relates to a kit of parts for making a cavity with an open, macroscopic, perfusable, pre-defined 3D shape within a surface or substrate of the invention within a microdevice, the kit comprising:

1. a microdevice, according to the invention,
    2. a defined substrate or surface according to the invention;
    3. a storage device to create the said 3D cavity.

The storage device may comprise a path file or computer readable instructions that, when executed controls a device to create the 3d cavity.

The microdevice and substrate may be provided as in the kits above. The storage device is preferably a memory stick.

EXAMPLES

Example 1. Formation and Characterization of Intestinal Organoids of Controlled Geometry 1.1. Introduction The macroscale epithelial geometry of organs such as the mammary gland has been shown to contribute toward its patterning and morphogenesis, by establishing regional differences in biochemical and mechanical signals (Gjorevski and Nelson, 2010; Shyer et al., 2015). The epithelial-mesenchymal geometry of the intestinal mucosa likewise helps to refine the spatial gradients of paracrine signals that ultimately separate the crypt and villus regions. However, the very existence of the highly patterned intestinal organoids strongly suggests that the epithelium itself is capable of self-organization, even in the absence of mesenchymal morphogenetic centers.

The inventors have observed that, upon organoid formation from previously spherical ISC colonies that express Lgr5 uniformly, Lgr5 is first downregulated globally, and re-expressed robustly and locally only after the crypt-like buds have formed. Preventing bud formation through mechanical confinement of the colonies blocks the re-expression of Lgr5 and the establishment of a localized stem cell zone, leading ultimately to colony destruction. Thus, the inventors postulated that the shape of the crypt represents an integral part of the ISC niche, helping to restrict the ISC zone and establish the crypt-villus axis. To test this hypothesis, they set out to build intestinal tissues of pre-defined size and geometry that mimic those of the crypt, and monitor how the initial shape affects the spatial distributions of ISC and the various differentiated cell types within the tissue.

1.2. Results 1.2.1. Formation of Intestinal Organoids of Controlled Geometry

Figure 1:
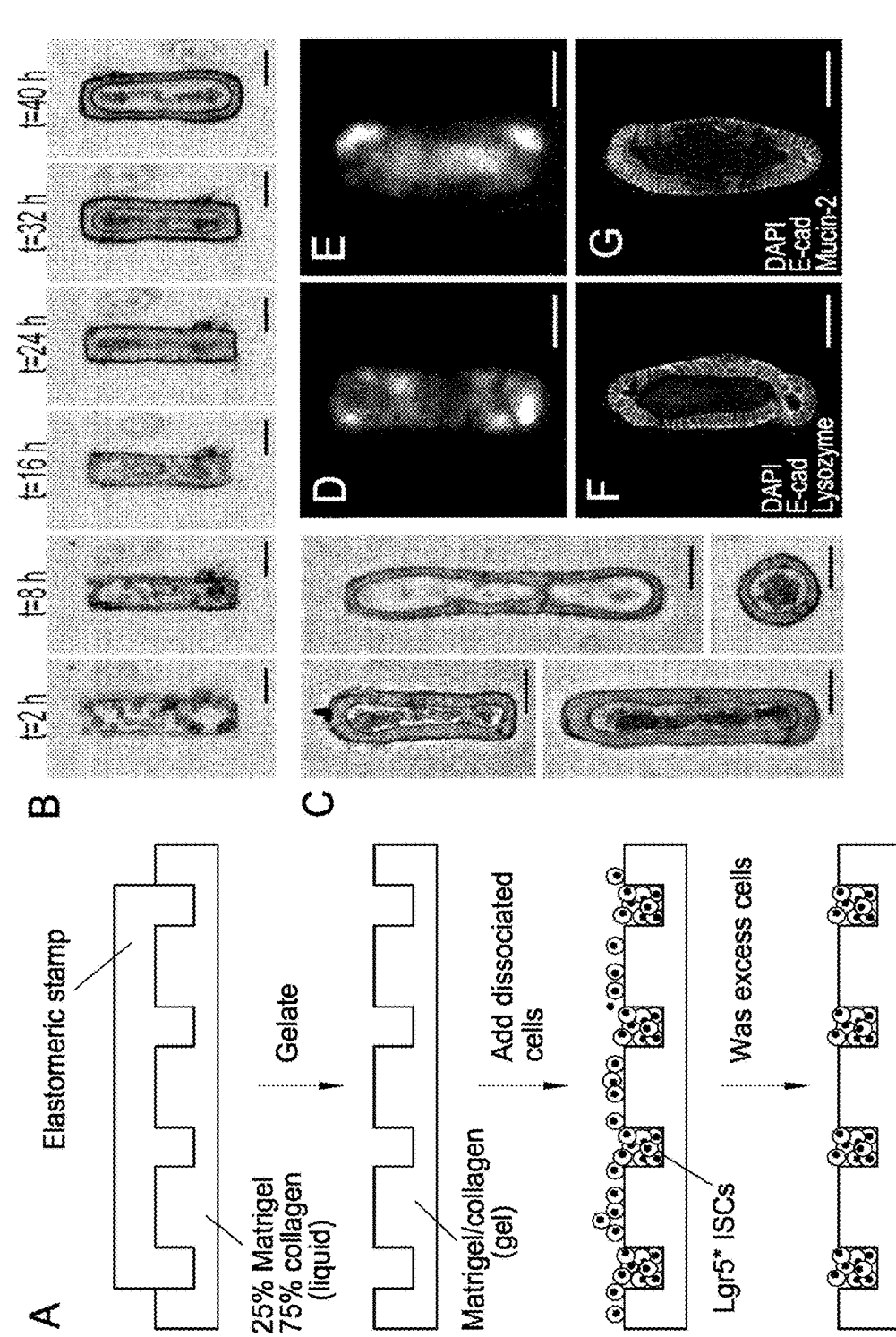
FIG. 1 Microfabricated intestinal tissue arrays.

To produce intestinal tissues of a desired geometry, a microfabrication approach was used. Briefly, hybrid gels comprising collagen type I and Matrigel were microstructured with an elastomeric stamp to generate cavities of controlled shape and size. The cavities were subsequently filled with dissociated Lgr5-EGFP-expressing mouse ISCs (FIG. 1A). Initially randomly dispersed, the stem cells began to form contacts with each other and the surrounding matrix, and within 48 h self-organized into a lumenized epithelial tissue conforming to the shape of the pre-existing cavity (FIG. 1B). This method was used to form intestinal tissues of arbitrary sizes and shapes (FIG. 1C). The crypt-like tubules formed by culturing the cells under self-renewal conditions expressed Lgr5-EGFP throughout (FIG. 1D). Upon switching to differentiation conditions, the Lgr5-EGFP signal became restricted to discrete locations (FIG. 1E), and differentiated intestinal cells (Paneth and goblet cells) appeared within the tissue (FIG. 1F, G). Thus, intestinal organoids of controlled geometry were successfully formed.

1.2.2. The Differentiation Pattern of Engineered Intestinal Tissue of Controlled Geometry Next the inventors sought to determine whether the differentiation of the engineered intestinal tissue followed a pattern or occurred randomly. The method described above generates hundreds of regularly spaced tissues of identical size and shape, which permits rapid imaging of fluorescent markers or proteins visualized by immunofluorescence analysis. Stacking images of a high number (>30) individual tissues in registration provides information about the average distribution of the molecule of interest, with high statistical confidence.

Using this approach, it was found that the Lgr5-EGFP signal was distributed uniformly across intestinal tissues formed from ISCs under self-renewal conditions (FIG. 2A, B). However, when switched to differentiation and organoid formation conditions, the Lgr5-EGFP signal became restricted to the curved ends of the tissues (FIG. 2C, D), indicating that ISCs are confined to these regions, in a pattern reminiscent to that seen in the native crypt. Importantly, the spatial patterning of Lgr5 expression was specific to the tissues of anisometric, non-circular geometry: no spatial bias in the localization of ISCs was observed in circular tissues, in either self-renewal or differentiation conditions (FIG. 2E-H). Intestinal tissues cultured under organoid formation conditions proceeded to extend crypt-like buds, as previously observed in classic intestinal organoid culture (Sato et al., 2009). The pattern of bud formation within the crypt-like tissues reflected that of the Lgr5 expression: the curved ends of the tissues were significantly more likely to extend buds than the flat sides (FIG. 2I-K). Immunofluorescence analysis for Paneth and goblet cells revealed that the former are preferentially localized to the same end locations as the ISCs (FIG. 2L, M), whereas the latter are on average excluded from the ends and confined to the middle of the tissue (FIG. 2N, O). Thus, the spatial distribution of ISCs and differentiated cells within the engineered tissues reflects the spatial pattern observed along the crypt-villus axis in vivo.

1.3. Discussion

Stem cell-derived organoids are superior tissue and organ mimetics that hold promise as models of human organ development and disease, platforms for drug discovery and design of personalized therapies, and as means to repair diseased and damaged tissue in the clinic. However, whereas the self-organization principles that drive their formation endow them with a high degree of complexity and fidelity to real organs, complementing self-organization with extrinsic regulation may afford better control over the course of organoid formation, thus expanding their utility in basic and clinical research. Here, the inventors show that microfabrication approaches can be used to form organoids of a desired geometry, and that the initial geometry of these structures dictates their subsequent morphogenesis.

The self-organizing and tissue-genic properties of dissociated epithelial stem cells and epithelial cells, in general, are long recognized (Lancaster and Knoblich, 2014; Sasai et al., 2012). Here the inventors demonstrate, however, that when the free boundary of a self-organizing cohort of ISCs is replaced with a physical yet biofunctional (adhesion-presenting) barrier, the shape of the resulting tissue can be controlled. Moreover, it was surprisingly found that the shape of thus engineered tissues can serve as a template for their patterning and further development. Specifically, it was found that the cellular patterning of the intestinal crypt could be replicated and aspects of the crypt-villus axis controlled by simply confining an initially uniform population of dissociated ISCs into a crypt-like geometry. These principles provide a powerful method to combine the self-organizing nature of organoids and their histological complexity with a level of extrinsic control that renders an otherwise stochastic developmental process more deterministic and guided. While the approach has been used here to engineer intestinal tissue of desired shape and control its patterning and subsequent budding, the method is readily adaptable to steer the development of other types of stem-cell derived organoids. Tubular tissues, including the neural tube, the lung, kidney, mammary gland and pancreas, seem particularly suitable.

In addition to providing a tool for guiding stem cell-based organoid formation, this work uncovered novel mechanisms of intestinal tissue patterning and morphogenesis that may potentially participate in the establishment of the crypt-villus system in vivo. A recent study showed that the shape of the intestinal villi leads to the local concentration of epithelial Shh signals. Shh then induces mesenchymal production of BMP4, which in turn locally suppresses Wnt signaling within the epithelium, thus restricting stem cells to the base of each villus[14]. Here, the inventors demonstrate that ISC restriction to the ends of crypt-like engineered tissue occurs in the absence of villi and mesenchyme, suggesting an additional mechanism for intestinal regionalization, whereby the epithelial geometry allows for autonomous patterning of the epithelium.

1.4. Materials and Methods 1.4.1. Mice

Intestinal crypts were extracted from 5-10 week old heterozygous Lgr5-EGFP-IRES-CreERT2 mice (Jackson Laboratory), following animal experimentation protocols prescribed by EPFL and FELASA.

1.4.2. Intestinal Crypt Isolation

Mouse intestinal crypts were isolated following previously established protocols (Wang et al, *Gastroenterology* 2013). Briefly, the proximal part of the intestine was harvested, opened longitudinally and washed with ice-cold PBS. The luminal side of the intestine was scraped with a glass slide to remove villi, and the intestine was cut into 4 mm pieces, which were washed with ice-cold PBS 5-10 times. To release the crypts, the intestinal fragments were incubated in 20 mM EDTA/PBS (20 min on ice). EDTA was removed, the fragments were resuspended in 10 ml of cold PBS was added, and shaken manually for 5 min to release the crypts into the suspension. The supernatant was collected and filtered through a 70-µm strainer (BD Biosciences). The resulting crypt-enriched suspension was centrifuged at 800 rpm for 5 min. The pellet was resuspended in 10 ml cold Advanced DMEM/F12 (Invitrogen) and centrifuged at 700 rpm to remove single cells and tissue debris. The resulting pellet was enriched in crypts, which were subsequently dissociated or directly embedded in PEG or in Matrigel™ (BD Biosciences; growth factor reduced, phenol red-free formulation). To produce a single cell suspension, crypts or ISC colonies were dissociated enzymatically by incubating for 8 min at 37° C. in 1 ml TrypLE Express (Life Technologies), supplemented with supplemented with DNAse I (2000 U/ml; Roche), 0.5 mM N-acetylcysteine (Sigma) and 10 µM Y27632 (Stemgent). The digested suspension was filtered using a 40 µm strainer to remove cell clumps and undigested crypt fragments.

1.4.3. Engineered Intestinal Microtissues

Elastomeric PDMS stamps containing defined features were treated with 1% BSA to prevent protein adhesion. A microstructured collagen-Matrigel gel was generated by polymerizing a liquid solution containing 3 mg/ml collagen (Koken) and 25% Matrigel (v/v) (Corning) around the stamp. After stamp removal, a concentrated suspension of Lgr5-EGFP-expressing mouse ISCs was placed onto the gel surface. The cells were allowed to enter the cavities, and the excess cells were washed gently with ice-cold Advanced DMEM/F12 (Invitrogen). The cells were sealed from the top with a second layer of collagen-Matrigel gel, and overlaid with ISC expansion medium.

1.4.4. Cell Culture

The microfabricated ISC arrays were allowed to self-organize into tissue by culturing them in ISC expansion medium (Advanced DMEM/F12 containing Glutamax, HEPES, penicillin-streptomycin, B27, N2 (Invitrogen) and 1 □M N-acetylcysteine (Sigma)), supplemented with growth factors, including EGF (50 ng/ml; R&D), Noggin (100 ng/ml; produced in-house) and R-spondin (500 ng/ml; produced in-house), and small molecules, including CHIR99021 (3 µM; Millipore), valproic acid (1 mM; Sigma) and thiazovivin (2.5 µM; Stemgent) for 2 d. To induce differentiation and organoid formation, the expansion medium was removed, the arrays were washed with PBS and medium containing only EGF, Noggin and R-spondin at the above concentration was added.

1.4.5. Immunofluorescence Analysis

Microfabricated intestinal tissues were fixed with 4% paraformaldehyde in PBS (30 min, RT), washed once with PBS, permeabilized with 0.2% Triton X-100 in PBS (1 h, RT) and blocked (10% goat serum in PBS containing 0.01% Triton X-100) for at least 3 h. The samples were incubated overnight at 4° C. with primary antibodies against lysozyme (1:50; Thermo Scientific PA1-29680), mucin-2 (1:50; Santa Cruz sc-15334) diluted in blocking buffer. After washing with PBS for at least 3 h, samples were incubated overnight at 4° C. with secondary antibody Alexa 647 goat-anti-rabbit (1:1000 in blocking solution; Invitrogen). Following multiple washes with PBS, stained microtissues were imaged in epifluorescence (Zeiss Axio Observer Z1) or confocal (Zeiss LSM 710) mode.

1.4.6. Frequency Maps

To generate frequency maps showing the average distribution of a molecule, multiple (>30) tissues in which the molecule was fluorescently visualized were imaged, the images binarized and stacked in registration using the ImageJ software. The resulting grayscale maps were converted into heat maps in Adobe Photoshop CS6.

Example 2. Intestinal Tubes 2.1. Results
2.1.1. Intestinal Tube Microdevice Design Although a variety of culture systems have been described, no developmentally relevant long-term culture system has been established that maintains the basic intestinal physiological architecture. The intestinal tube microdevice was designed to create intestinal tissues with a tubular physiological geometry in an in vitro organotypic system.

The intestinal tube system consists of three compartments: a matrix compartment flanked by two media reservoirs (FIG. 3A). The central matrix compartment contains a 3D ECM mainly composed of Matrigel, a laminin-rich naturally derived matrix that supports both intestinal epithelial growth and differentiation (Barker et al., 2007; Sato et al., 2009). Matrigel-based cultures have been successfully used for the growth of other organotypic models from stem cells, such as the optic cup (Eiraku et al., 2011) and the mini-brain (Lancaster et al., 2013).

To induce the formation of a tube-shaped intestinal epithelial sheet from ISCs that matches the physiological geometry of the developing intestine (Shyer et al., 2015), a 3D parallelepiped microtrack was generated within the matrix by laser ablation (FIG. 3B). Due to the low stiffness of Matrigel (elastic modulus of approx. 450 Pa (Soofi et al., 2009)), a minimum of 10% (v/v) collagen type I content, the major component of the stromal ECM, was added to the Matrigel to allow structural stabilization of laser ablated microtrack. In the absence of collagen or when present in lower amounts, laser ablated microtracks collapsed within minutes.

On the other hand, collagen contents higher than 15% are not compatible with crypt formation or differentiation of ISCs. Laser ablating a rectangular pattern of consecutive parallel lines from one extremity of the matrix compartment to the other resulted in the creation of a microtrack devoid of matrix that connects the chamber's inlet and outlet. The number of lines defined the microtrack width (usually between 70 and 100 μm). The laser focal volume was set at 100 μm above the glass bottom of the microdevice. Nevertheless, due to the biconical shape of the laser beam, matrix was also ablated several microns below and above the laser focal plane. This depth was proportional to the laser power used. The resulting microtrack covering the entire length of the matrix compartment, creates a channel through the 3D ECM (FIG. 3B).

To effectively examine the geometry and size of the channel, fluorescently-labelled Dextran (2000 kDa) was added to the cell's inlet and allowed to enter a 100 μm width laser ablated microtrack by gravity induced flow. Confocal imaging of the fluorescent dye showed a rectangular prism shaped hollow tube, with 155 μm width (xy view) by 140 μm depth (xz view) (FIG. 3C). Differences between the laser ablated width and the effective one are due to the viscoelastic properties of the matrix. Nevertheless, channels showed a precise medium-matrix interface and were largely free of debris inside the lumen (FIG. 3B), thus representing a defined model for 3D microtrack formation within a physiological substrate as a border to support cell adhesion and geometrically guided development.

The media reservoirs were used as source of nutrients and diffusive signals. Molecules diffuse through the 3D matrix compartment resulting in a passive formation of gradient concentration profile. Fluorescently labeled 40 kDa dextran was used to visualize the gradient and track its stability over 2 days while reservoirs were not replenished (FIG. 3C-E). The equilibrium profile is reached within a day with about 2 fold difference between the two extreme regions of the matrix chamber. Fluorescence intensity was normalized to the source and the molecular concentration within the chamber was ranging from 20% to 60% relatively to the source concentrations. The high baseline concentration is probably due to unspecific interaction of dextran with the collagen gel. Good stability of the profile is guaranteed once the equilibrium is reached. Gradient profile is strongly dependent on diffusivity of the molecules through the porous structure of the gel. Indeed, the open region of the reservoir is not directly adjacent to the chamber part: gaps of about 300 μm must be ensured between the two compartments due to practical reasons of the manufacturing step. Gaps result in unexploitable gradient regions that restrict the effective range of the gradient. This gap effect affects more small molecules that have similar diffusivity in aqueous and gel phases than larger molecules.

2.1.2. Culturing ISCs as Intestinal Tubes

Lgr5-GFP+ ISCs, originated from Lgr5-EGFP-IRES-Cre-ERT2 mice and cultured in vitro as ISC colonies under self-renewal conditions, were added to the microdevice cells' inlet as a highly dense single cell suspension and allowed to enter the microchannels by gravity induced flow. During the first 24 hours in self-renewal conditions (ENRCV media), ISCs that have adhered to the walls of the laser ablated microchannel, proliferate and start to self-organise into several consecutive cyst-like structures, with epithelial monolayers surrounding a lumen, similar to intestinal organoids (FIG. 4A, 24 hrs). After 2 days, as ISC proliferation is strongly induced under self-renewal conditions, the epithelial sheets start to invaginate outwards, towards the ECM (FIG. 4A, 48 hrs). Over time, cyst-like structures fuse with each other, creating a continuous intestinal tube-shaped epithelium arranged around a central lumen (FIG. 4A, 72 hrs).

To induce differentiation of ISCs organised as epithelial tubes, cells were exposed to differentiation conditions by replacing the self-renewal media in the media reservoirs with differentiation media (ENR media). Switching to differentiation conditions prompted radial extension of multiple crypt-like structures from the intestinal tube-shaped epithelium (FIG. 4A, 72 hrs). After 3 days under differentiation conditions, the number and size of crypts extending towards the ECM had greatly increased and covered the entire length of the intestinal tubes (FIG. 4C). Multiple Lgr5-EGFP cells were found to restrictively localised at the crypt bottoms (FIG. 4B), as it has been described in intestinal organoids (Sato et al., 2009) and in vivo (Barker et al., 2007; Shyer et al., 2015). Multipotency of ISCs was confirmed by immunostaining with specific markers for three types of differentiated intestinal cells: Paneth, Goblet and enteroendocrine cells (Barker et al., 2007) (FIG. 5). Paneth cells (lysozyme staining) were mostly localised to crypt bottoms, whilst Goblet cells (mucin 2 staining) and enteroendocrine cells (chromogranin A) were scattered throughout the intestinal tubes and excluded from crypt bottoms. Altogether, these results show that ISCs grown in a 3D matrix engineered with a predefined tubular geometry are able to self-organise into tube-shaped intestinal epithelia and give rise to intestinal differentiated cells with the same spatial distribution found in vivo.

2.1.3. Geometrically Guided Self-Organization of mISCs into Tubular Organoids

Previously we have demonstrated the development of the tubular organoid by self-organisation of mouse intestinal stem cells in a laser-ablated tube within the gel-loaded microdevice. Here, using laser-ablation to generate tubes with additional cavities within a hydrogel matrix, we further develop this concept and demonstrate that stem cells can be coaxed to form crypts of a defined shape and size.

To restrict spontaneous crypt formation 20% Matrigel/ 80% type I collagen gel (approx. 1000 Pa) was chosen. Laser-etched microchannel at the centre of the hydrogel feature special cavities protruding outwards, mimicking the geometry of the intestinal crypts. The diameter of the microchannel was approximately 130 μm, cavities were 150 μm deep and 50 μm wide (FIG. 7A). Lgr5-eGFP+ ISCs were pipetted into the cell inlet of the chip as a highly concentrated single cell suspension. After 1 h, non-adherent cells were washed off leaving only small cell colonies in the cavities. During the first 24 hours, cells settled down in the cavities and confluently covered the surface of the engineered substrates. Within the following 12 hours, cells cover the whole surface of the tube with confluent monolayer (FIG. 7A). During first 36 hours, we kept self-renewal media both inside the tube and in the reservoirs, and observed that Lgr5-eGFP+ cells were randomly distributed along the tube. After completion of tube formation, the chip was connected to the microfluidic pumps to allow continuous perfusion of the lumen and removal of dead cells. Then, to induce differentiation of ISCs, cells were exposed to differentiation conditions by replacing the self-renewal media in the media reservoirs with differentiation media (ENR media), which resulted in differentiation of epithelial cells in the lumen with the majority of cells in the crypts being LGR5-eGFP positive (FIG. 7B).

After 5-6 days (2-3 days in self-renewal conditions+3 days in differentiation conditions) we investigated the cellular composition and architecture of the intestinal tubes. Samples were fixed and immunostained by antibodies to SOX9, lysozyme and L-FABP to visualize stem/progenitor cells, Paneth cells and enterocytes, respectively.

We found that enterocytes were localized preferentially in the lumen, whereas the Paneth cells preferentially localized to the crypt regions (FIG. 7C). The presence of Paneth cells in the crypt regions is also consistent with their niche function to maintain of stem cells and secrete microbial defense molecules such as defensins and lysozyme.

2.1.4. Human iPS Cells Culture in the Tube-Shaped Matrix Microtrack

Our approach to guide self-organisation of intestinal stem cells into tissues of pre-defined shape can be extended to cells of different origin. As additional example, we demonstrate the formation of tubular organoids from human iPS cells (FIG. 8).

2.2. Discussion

Microfabrication is allowing researchers to structure space at the right order of scale for positioning individual cells according to architectures experienced in vivo. Microfluidics also provides new tools for controlling the transport and availability of biochemical signals on such micron scales. Here the inventors use microfabrication combined with 3D matrix microstructuring and microfluidics to create a new intestinal organotypic culture system derived from ISCs.

ISCs grown in a 3D matrix engineered with a predefined tubular geometry are able to self-organise into tube-shaped intestinal epithelia and give rise to intestinal differentiated cells with the same spatial distribution found in vivo. The generation of a tube-shaped epithelial sheet from ISCs in a well-defined spatial position, not only matches the physiological sheet geometry of the developing intestine, but also allows high-resolution time-lapse imaging of individual cells, in opposition to the matrix scattered, highly mobile spheroid organoids. This will help elucidating about cellular modifications in shape, polarization and migration, as well as the underlying cellular mechanisms that occur during intestinal development. Understanding the mechanisms that govern normal intestinal development is critical, as it may provide insight into how they are subverted during pathologies of the intestinal system, including colorectal cancer.

Furthermore, since the intestinal tube covers the entire length of the matrix compartment, connecting the cells' inlet and outlet, it creates the possibility of accessing to the intestinal lumen by microfluidic perfusion. Perfusion of the intestinal tubes will allow clearance of shed dead cells resulting from the normal intestinal regeneration and, more importantly, will open unprecedented opportunities to study intestinal drug absorption and metabolism, as well as symbiotic or pathogenic interactions with intestinal bacteria. Finally, the use of microfluidics permits perfusion at low rates, matched to those observed in vivo. Biomolecules diffuse away from the media reservoirs into the permeable ECM, forming a gradient with a spatial and temporal profile that can be controlled by modifying the media composition within the reservoirs and used to guide intestinal morphogenesis and organogenesis in culture.

This model system has therefore a high physiological significance and is the perfect tool to address questions related to intestinal development and homeostasis, with potential applications in regenerative medicine, drug metabolism and colorectal disease therapy.

2.3. Materials and Methods 2.3.1. Microdevice Design and Mask Fabrication

The microdevice is composed of three main compartments: a 3D matrix chamber and two media reservoirs. A 800 μm-wide and 2 mm-long central matrix chamber is sandwiched by two 4 mm-wide open media reservoirs. Matrix chamber is connected to a pair of inlet/outlet for cell loading and an extra inlet from which the matrix is loaded. Compartments are partitioned by 120 μm-wide phase-guiding features that enable loading compartments separately with dedicated materials without spillage. Phase-guiding features consist of semi-walls shielding the top 240 μm height combined with pillars covering the entire height. Additional 120-wide channels were placed between the matrix chamber and medium reservoirs to remove residual air after the complete polymerization of the 3D matrix.

The device layout was drawn with dedicated software (CleWin, Phoenix Software) and printed on a glass mask via high-resolution laser-based method. Briefly, the designed layout was written with diode laser with 2000 nm-resolution onto a glass plate coated with chrome and positive photoresist (Nanofilm) using dedicated automated system (VPG200, Heidelberg instruments). Unexposed photoresist was then removed with a developer (DV10, Süss MicroTec) and then the underneath chrome layer was etched with an acid/oxidizer solution of perchloric acid, cerium ammonium nitrate and water. Finally the resulting mask was developed with TechniStrip P1316 (Microchemicals) to remove the residual resist and extensively washed with ultra-pure water.

2.3.2. Soft Lithography and PDMS Moulding

The microfabricated platform was fabricated using conventional soft-lithography methods and poly(dimethylsiloxane) (PDMS) moulding. The mould was made from multiple-layered epoxy-based negative photoresist SU8 with dedicated design (FIG. 1a) described in the next paragraph. 240 μm thick layer of SU8 GM1075 (Gerlteltec) photoresist was cast onto a dehydrated silicon wafer using a negative resist coater (LMS200, Sawatec). The wafer was then aligned and exposed to UV through the first mask (MA6/BA6, Süss MicroTec). After baking at 95° C., a second layer of SU8 GM1075 was spin coated as previously and exposed to UV through the second mask, carefully aligned using dedicated alignment marks. After the post-exposure bake, the wafer was developed with Propylene glycol monomethyl ether acetate (Sigma) and baked again at 135° C. overnight. The thickness of the total SU8 layer was confirmed with a surface profilometer (Dektak XT, Bruker). The wafer was then plasma-activated and silanized with vapored Trichloro (1H, 1H, 2H, 2H-perfluorooctyl) silane (Sigma) for overnight.

The microstructured wafer was then utilized for moulding PDMS (Sylgard 184, Dow Cornging). 10 weight-parts of elastomer base was vigorously mixed with 1 part of curing agent and poured onto the mould. After degassing under vacuum, PDMS was baked in an oven for 24 hours at 70° C. The resulting PDMS replica was cut and punched with appropriate size of biopsy punchers (Kai medical). PDMS chips were then soaked in a series of organic solvents to remove the unreacted PDMS macromers. PDMS chips were subsequently soaked under stirring in trimethylamine (Millipore) for 4 hours, in ethyl acetate (Sigma) for 4 hours and then in acetone (VWR chemicals) for 48 hours while renewing the bath every 12 hours. The resulting PDMS chips were briefly exposed to oxygen plasma and irreversibly bonded onto a glass substrate. Chips were sterilized with UV and kept in the 37° C. and humidified incubator prior to use.

2.3.3. Cell Culture

Lgr5-GFP+ ISCs, extracted from Lgr5-EGFP-IRES-Cre-ERT2[5] mice and purified using flow cytometry for single GFP[hi] cells were routinely cultured as ISCs colonies embedded in Matrigel (BD Bioscience) and under self-renewal conditions (ENRCV media[8]: Advanced DMEM/F12 media (Invitrogen) supplemented with 1× Glutamax, 10 mM HEPES, 100 units/ml penicillin+100 μg/ml streptomycin (Gibco), 2% (v/v) B27 supplement (Gibco), 1% (v/v) N2 supplement (Gibco), 1 μM N-acetylcysteine (Sigma-Aldrich), containing growth factors 50 ng/ml EGF, 100 ng/ml Noggin, 1 μg/ml R-spondin1 (EPFL Protein Expression Core Facility) and small molecules 3 μM CHIR99021 (Stemgent) and 1 mM valproic acid (Sigma-Aldrich)). Growth factors and small molecules were added every other day and the entire medium changed every 4 days. For passage, ISCs colonies were removed from Matrigel and mechanically dissociated into smaller colonies, and then transferred to fresh Matrigel. Passage was performed every week with a 1:4 split ratio. ISCs were maintained at 37° C. in 5% $CO_2$ humidified air during culture.

2.3.4. Matrix and Matrix Laser Microstructuring

An ECM solution containing 10% (v/v) native bovine dermis collagen type I solution (5 mg/mL stock concentration neutralised and reconstituted with Advanced DMEM/F12 media to a 4% solution according to the manufacturer's protocol (Kouken)) and 90% (v/v) Matrigel was injected into the matrix compartment of the microdevice by the matrix loading inlet and incubated at 37° C. for 5 min, after which the cell loading inlet and outlet were filled with ENRCV media.

Generation of microtracks ablated in 10% Collagen/90% Matrigel 3D ECMs was performed using a nanosecond laser system (1 ns pulses, 100 Hz frequency, 355 nm; PALM MicroBeam laser microdissection system (Zeiss)) equipped with a 10×/0.25NA objective. A rectangular pattern of consecutive parallel lines was created in Adobe® Illustrator® CS6 and then converted to the microscope specific format using a custom-made converter before importing into the PALM MicroBeam system's interface. Rectangular regions of interest of 2500 μm length by 70 or 100 μm width were positioned along the microdevice matrix compartment, covering its entire length, at Z=100 μm from the glass surface. Following microtrack generation, microdevices were maintained at 37° C. in 5% $CO_2$ humidified air.

2.3.5. Intestinal Tubes

For single-cell dissociation, ISCs colonies were removed from Matrigel and dissociated with TrypLE express solution (Invitrogen) containing 2,000 U/ml DNaseI (Roche), 1 mM N-acetylcysteine and 10 μM Y27632 for 8 min at 37° C. Dissociated cells were passed through 40 μm cell strainer (Falcon) and resuspended in ENRCV media containing 2.5 μm Thiazovivin (Stemgent) at density of $10^6$ cells/ml. After removing the media from both cell inlet and outlet of the microdevice, 5 μl of cell suspension was added to the cells' inlet and cells were allowed to fill the laser ablate microtrack by gravity driven flow. Within the first minute, cell flow was maximal and most cells entered the channel during this time. As the cells' inlet and outlet volumes balance, the flow decreases until it stopped after about 10 minutes. At this time, the microchannel is heavily packed with single ISCs. Microdevice media reservoirs were then filled with 50 μl of ENRCV media+2.5 μm Thiazovivin and placed at 37° C. in 5% $CO_2$ humidified air. After 2 hrs, unattached ISCs were washed out from the microdevice cell inlet and outlet with ENRCV media+2.5 μm Thiazovivin and placed again at 37° C. in 5% $CO_2$ humidified air.

After 2 days, media in the microdevice media reservoirs and cells' inlet and outlet was replaced by differentiation media (ENR media[5,9]: Advanced DMEM/F12 media (Invitrogen) supplemented with 1× Glutamax, 10 mM HEPES, 100 units/ml penicillin+100 μg/ml streptomycin (Gibco), 2% (v/v) B27 supplement (Gibco), 1% (v/v) N2 supplement (Gibco), 1 μM N-acetylcysteine (Sigma-Aldrich) and containing growth factors 50 ng/ml EGF, 100 ng/ml Noggin, 1 μg/ml R-spondin1 (EPFL Protein Expression Core Facility)) and ISCs were allowed to differentiate for 3 days at 37° C. in 5% $CO_2$ humidified air.

2.3.6. 3D Immunofluorescence Staining

Intestinal tubes were fixed in 4% PFA for 30 minutes at room temperature. After rinsing with PBS, cells were permeabilised with 0.2% Triton X-100+1% BSA in PBS for 1 hr at room temperature with agitation. After rinsing with PBS, cells were incubated with primary antibodies against Lysozyme (Pierce), Mucin2 (Santa Cruz) and chromogranin A (Santa Cruz) diluted in PBS overnight, at 4° C. Cells were washed 3×1 hr with 0.05% Tween 20 in PBS followed by incubation with the appropriate Alexa-conjugated secondary antibody, Alexa-conjugated phalloidin and DAPI (Molecular Probes) diluted in PBS overnight, at 4° C. Cells were further washed 3×1 hr with 0.05% Tween 20 in PBS, with agitation, before addition of mounting media (Prolong Diamond, Molecular Probes).

2.3.7. Microscopy and Imaging Processing

Intestinal tubes were imaged with an inverted confocal microscope (INVERT Zeiss AxioObserver Z1) equipped with 10×/0.30NA and 20×/0.80NA air objectives, 405 nm, 488 nm and 555 nm lasers and controlled by ZEN 2009 imaging software (Zeiss). Z slices were acquired at 10 or 4 μm intervals. Z stacks were maximally projected using ImageJ (open source) to create 2D images and further processed using Photoshop CC (Adobe) using only standard contrast and intensity level adjustments.

2.3.8 Human iPS-Derived Intestinal Organoids Cell Culture

Human iPS-derived intestinal organoids were generated as described previously described [Hannan, N. R. et al. Generation of multipotent foregut stem cells from human pluripotent stem cells. Stem cell reports 1, 293-306, doi: 10.1016/j.stemcr.2013.09.003 (2013)]. Briefly, organoids were maintained and expanded as follows in full expansion medium (hIO media) composed of Advanced DMEM/F12 containing Glutamax, HEPES, penicillin/streptomycin, N2 (Life technologies), B27 (Life technologies), N-acetylcysteine (1 mM; Sigma), EGF (50 ng/ml; R&D), Noggin (100 ng/ml; produced in-house) and R-spondin (500 ng/ml; produced in-house), Nicotinamide (10 mM, Sigma), A83-01 (500 nM, Tocris), Prostaglandin-E2 (2.5 µM; Tocris), Wnt3A (100 ng/ml; R&D) and Y-27632 (10 µM, Abmole). Medium was changed every 2-3 days and cells were passaged every 7-10 days.

To prepare samples, human iPSC colonies were removed from Matrigel and dissociated into single cells with TrypLE express solution (Invitrogen) containing 2,000 U/ml DNaseI (Roche), 1 mM N-acetylcysteine and 10 µM Y27632 for 8 min at 37° C. Dissociated cells were passed through 40 µm cell strainer (Falcon), centrifuged at 1000 rpm for 4 min, and then resuspended in hIO media at density of $10^6$ cells/ml. After removing the media from the microdevice cell inlets, 5 µl of cell suspension were added to each inlet and cells were allowed to fill the laser ablated microtrack by gravity driven flow. Within the first minute, cell flow was maximal and most cells entered the microtrack during this time. After 10 minutes, the microtrack is heavily packed with single cells. The media reservoirs were then filled with hIO media and the microdevice was placed at 37° C. in 5% CO2 humidified air. After 1 hour, unattached cells were washed out from the cell inlets and microtrack by flowing hIO media and the microdevice was again placed at 37° C. in 5% CO2 humidified air. During the first 48 hours, cells settled down in the cavities and confluently covered the surface of bioengineered niches. Within the following days, cells covered the whole surface of the tube with confluent monolayer (FIG. 8).

Example 3. Engineering Intestinal Surfaces 3.1. Introduction

Functionally relevant modelling of intestinal diseases is improved by appropriate modelling of the continuous interaction between intestinal epithelial cells and other intestinally resident cells such as immune cells and components of the microbiome. The modelling of such interactions requires a continuous monolayer of epithelial cells.

One study attempted to produce such a monolayer by culturing ISCs on the ECM-coated surface of a transwell insert (Wang et al., 2015). However, the cells in these cultures failed to cover the entire surface of the membrane so as to form a continuous monolayer.

3.2. Results 3.2.1. Formation of a Continuous Layer of ISCs

The inventors hypothesized that in order to form a continuous monolayer on a surface, ISCs would need to form cell-cell contacts within the first few hours of being seeded onto the surface in order to avoid cell death and/or differentiation. The inventors therefore seeded ISCs onto a Matrigel surface at a very high density so that neighboring cells could establish contacts immediately after seeding. This produced a layer of cells that survived for up to 4-6 days and spontaneously began to form sporadic crypt-like invaginations (FIGS. 5A and 5B).

3.2.2. Formation of a Continuous Layer of Cells with an Intestine-Like Micro-Topology This method was then combined with the topographical approach described in Examples 1 and 2. In particular, ISCs were seeded at high density into microwells possessing micro-topography mimicking the stem cell niches of the intestines (FIG. 5C). An example topographical structure is shown in FIG. 5D. Cells were seeded at high density onto hydrogels possessing intestine-like micro-topography (FIG. 5E) and cultured under proliferating conditions for 1-2 days until they covered the entire surface of the hydrogel. The culture was then switched to differentiation conditions. LGR5-GFP expression was still observed within the crypts following 2 days of culturing in differentiation conditions, demonstrating that the population of stem cells was maintained within the layer (FIG. 5F, G). In line with in vivo studies of intestinal cellular composition, the epithelium layer was primarily composed of enterocytes, interspersed with small populations of Goblet and enteroendocrine cells (FIG. 5G). The crypts also exhibited a classic intestinal crypt shape (FIG. 5H-J).

Screening of the different microwells diameters was performed to identify the influence of size on the self-organisation of the mISCs into crypts (FIG. 5K). On average, a significantly higher efficiency of crypt formation was found for microwells diameter in a range 45-55 µm, ISCs formed crypts in more than 75% of all microwells. For 40 µm microwells, we observed only 17% efficiency of crypts formation, for 30 µm only 11%.

Microwells larger than 60 µm are also unfavourable for crypt formation; only in a low number of microwells cells were able to penetrate the bottom of the microwell and form crypt-like structures within the matrix.

Stem cells can self-organize within 3D matrices into structures that capture several aspects of real tissues, but this capacity is limited to a microscopic level. That is to say, organoids obtained under exactly the same culture conditions are very heterogeneous in terms of their crypt numbers, size and shape. In adult organs, as well as during development process, (committed) stem cells are in crosstalk with surrounding tissues that guide their self-organisation on a macroscopic scale. Biochemical communication between neighbouring cells, via secretion of signalling molecules has been extensively studies. Apart of that, physical interactions between cells also play a crucial role in regulating organogenesis. Indeed, stem cells require external physical guidance to self-organise into properly organized, macroscopic and functional tissues. These findings, altogether with Example 1, suggest the important influence of the precise geometry on guiding stem cell self-organisation.

3.2.3. Engineered Intestinal Surface on a Microfluidic Chip

Various cell-based systems have been engineered for cultivating intestinal epithelium. In particular, transwell inserts have become a golden standard for studies of epithelial transport, absorption and secretion. In classical Transwell co-culture devices, a layer of confluent epithelial cells is grown on a porous membrane forming the bottom of a the transwell insert. The insert is placed inside a well of a 6, 12 or 24 well plate (FIG. 6A) and separates the culture medium in upper and lower compartments of the device. The insert thereby provides convenient and independent access to medium at both the apical and basolateral sides of the monolayer of cells.

Transwells provide a versatile tool with which to study transport across the monolayer. However, they are expensive and not suited to modelling the dynamically active microenvironments of the living intestine because they cannot be used to replicate the normal dynamic processes critical to normal gut physiology, including intralumenal fluid flow and peristaltic motions. The static nature of transwells also leads to the accumulation of waste and pH drift within the insert, preventing the culture of living microbes on the surface of the cellular layers for extended periods.

A micro-fluidic cell-based system can overcome these limitations and provides a better tool for fast and efficient nutrient absorption assays. However, these devices have only previously been used to grow epithelial cell lines, such as the human colorectal adenocarcinoma cell line Caco-2. Such cells lack the heterogeneity found in the intestinal mucosa, limiting their use in the study of intestinal disease and function. The inventors therefore designed a microfluidic chip for growing the engineered intestinal surfaces from ISCs as described in Example 4 (FIG. 6B).

REFERENCES

Abberton, K. M., Bortolotto, S. K., Woods, A. A., Findlay, M., Morrison, W. A., Thompson, E. W., and Messina, A. (2008). Myogel, a novel, basement membrane-rich, extracellular matrix derived from skeletal muscle, is highly adipogenic in vivo and in vitro. Cells Tissues Organs 188, 347-358.

Barker, N., van Es, J. H., Kuipers, J., Kujala, P., van den Born, M., Cozijnsen, M., Haegebarth, A., Korving, J., Begthel, H., Peters, P. J., et al. (2007). Identification of stem cells in small intestine and colon by marker gene Lgr5. Nature 449, 1003-1007.

Bhatia, S. N., and Ingber, D. E. (2014). Microfluidic organson-chips. Nat. Biotechnol. 32, 760-772.

Chassaing et al, (2014) Dextran sulfate sodium (DSS)-induced colitis in mice. Curr Protoc Immunol 104: Unit 15.25

Chen, Y., Lin, Y., Davis, K. M., Wang, Q., Rnjak-Kovacina, J., Li, C., Isberg, R. R., Kumamoto, C. A., Mecsas, J., and Kaplan, D. L. (2015). Robust bioengineered 3D functional human intestinal epithelium. Sci. Rep. 5, 13708.

Costello, C. M., Hongpeng, J., Shaffiey, S., Yu, J., Jain, N. K., Hackam, D., and March, J. C. (2014). Synthetic Small Intestinal Scaffolds for Improved Studies of Intestinal Differentiation. Biotechnol. Bioeng. 111, 1222-1232.

Eiraku, M., Takata, N., Ishibashi, H., Kawada, M., Sakakura, E., Okuda, S., Sekiguchi, K., Adachi, T., and Sasai, Y. (2011). Self-organizing optic-cup morphogenesis in three-dimensional culture. Nature 472, 51-56.

Eszlinger, M., Krohn, K., Hauptmann, S., Dralle, H., Giordano, T. J., and Paschke, R. (2008). Perspectives for improved and more accurate classification of thyroid epithelial tumors. J. Clin. Endocrinol. Metab. 93, 3286-3294.

Finkbeiner, S. R., Freeman, J. J., Wieck, M. M., El-Nachef, W., Altheim, C. H., Tsai, Y.-H., Huang, S., Dyal, R., White, E. S., Grikscheit, T. C., et al. (2015). Generation of tissue-engineered small intestine using embryonic stem cell-derived human intestinal organoids. Biol. Open 4, 1462-1472.

Gjorevski, N., and Nelson, C. M. (2010). Endogenous patterns of mechanical stress are required for branching morphogenesis. Integr. Biol. Quant. Biosci. Nano Macro 2, 424-434.

Hagenkord, J. M., Gatalica, Z., Jonasch, E., and Monzon, F. A. (2011). Clinical genomics of renal epithelial tumors. Cancer Genet. 204, 285-297.

Hannan, N. R. et al. Generation of multipotent foregut stem cells from human pluripotent stem cells. Stem cell reports 1, 293-306, doi:10.1016/j.stemcr.2013.09.003 (2013)

Lancaster, M. A., and Knoblich, J. A. (2014). Organogenesis in a dish: modeling development and disease using organoid technologies. Science 345, 1247125.

Lancaster, M. A., Renner, M., Martin, C.-A., Wenzel, D., Bicknell, L. S., Hurles, M. E., Homfray, T., Penninger, J. M., Jackson, A. P., and Knoblich, J. A. (2013). Cerebral organoids model human brain development and microcephaly. Nature 501.

Levin, D. E., Barthel, E. R., Speer, A. L., Sala, F. G., Hou, X., Torashima, Y., and Grikscheit, T. C. (2013). Human tissue-engineered small intestine forms from postnatal progenitor cells. J. Pediatr. Surg. 48, 129-137.

Madan, A. K., Weldon, C. B., Long, W. P., Johnson, D., and Raafat, A. (2004). Solid and papillary epithelial neoplasm of the pancreas. J. Surg. Oncol. 85, 193-198.

Metcalfe et al, (2014). Lgr5+ stem cells are indispensable for radiation-induced intestinal regeneration. Cell Stem Cell 14(2):149-59.

Mongens, R. D., Lotte, M., Jette, L., Annette, C. F., Ernst, M. F., Morten, F., Flemming, B., and Finn, S. P. (2014). Biocompatible Material for Mammalian Stem Cell Growth and Differentiation.

Nelson, C. M., Vanduijn, M. M., Inman, J. L., Fletcher, D. A., and Bissell, M. J. (2006). Tissue geometry determines sites of mammary branching morphogenesis in organotypic cultures. Science 314, 298-300.

Ramalingam, P. (2016). Morphologic, Immunophenotypic, and Molecular Features of Epithelial Ovarian Cancer. Oncol. Williston Park N 30, 166-176.

Rivron, N. C., Rouwkema, J., Truckenmuller, R., Le, G. S., Blitterswijk, C. A., Vrij, E. J., Rivron, N. C., Le, G. S., and Van, B. C. A. (2011). Self-Assembling Tissue Modules.

Sasai, Y., Eiraku, M., and Suga, H. (2012). In vitro organogenesis in three dimensions: self-organising stem cells. Dev. Camb. Engl. 139, 4111-4121.

Sato, T., Vries, R. G., Snippert, H. J., van de Wetering, M., Barker, N., Stange, D. E., van Es, J. H., Abo, A., Kujala, P., Peters, P. J., et al. (2009). Single Lgr5 stem cells build crypt-villus structures in vitro without a mesenchymal niche. Nature 459, 262-265.

Shyer, A. E., Huycke, T. R., Lee, C., Mahadevan, L., and Tabin, C. J. (2015). Bending gradients: how the intestinal stem cell gets its home. Cell 161, 569-580.

Soofi, S. S., Last, J. A., Liliensiek, S. J., Nealey, P. F., and Murphy, C. J. (2009). The elastic modulus of Matrigel as determined by atomic force microscopy. J. Struct. Biol. 167, 216-219.

Todhunter, M. E., Jee, N. Y., Hughes, A. J., Coyle, M. C., Cerchiari, A., Farlow, J., Garbe, J. C., LaBarge, M. A., Desai, T. A., and Gartner, Z. J. (2015). Programmed synthesis of three-dimensional tissues. Nat. Methods 12, 975-981.

Wang, X., Yamamoto, Y., Wilson, L. H., Zhang, T., Howitt, B. E., Farrow, M. A., Kern, F., Ning, G., Hong, Y., Khor, C. C., et al. (2015). Cloning and variation of ground state intestinal stem cells. Nature 522, 173-178.

The invention claimed is:

1. An in vitro method for obtaining an organoid having a pre-determined tissue shape and pattern, comprising:

i. seeding stem cells capable of differentiating to form the organoid in a three-dimensional (3D) structure within a macroscopic block of hydrogel, wherein said stem cells are isolated epithelial stem cells, and the 3D structure is a cavity within the macroscopic block of hydrogel, wherein the cavity forms a tube comprising two open ends that allow perfusion with liquid, and, wherein the tube comprises a longitudinal section along the longitudinal axis of the tube, wherein the section has a rectangular cross section, wherein the rectangle has sides that are between 10 μm and 5 mm in length, or the section has a circular or elliptical cross-section, wherein the ellipse has two principal axes between 10 μm and 5 mm in length, ii. culturing the stem cells under self-renewal conditions, wherein the stem cells proliferate and pattern to form a colony having the same 3D structure as the macroscopic block of hydrogel and cover the 3D structure in the macroscopic block of hydrogel, and iii. culturing the 3D structure of step (ii) covered with the colony of the stem cells in the presence of differentiation conditions such that the colony of the stem cells undergoes morphogenesis to form the organoid with reproducible and predictable shape and pattern, wherein the macroscopic block of hydrogel has a minimum elastic modulus of at least 450 Pa.

2. The method of claim 1, wherein the epithelial stem cells are small intestinal, stomach, colon, pancreatic, lung, prostate, mammary, corneal, hair follicle, epidermal cells or progenitors of such cells.

3. A method according to claim 1, wherein the 3D structure is obtained by replica moulding, soft embossing, injection moulding, 3D printing, bioprinting, laser machining, micromachining, surface etching, optical lithography, additive manufacturing, electrochemical directed crosslinking soft-lithography, and/or polydimethyl siloxane (PDMS) replica moulding.

4. The method of claim 1, wherein a hydrogel of the macroscopic block of hydrogel comprises:

i. naturally derived components, selected from the group comprising polysaccharides, gelatinous proteins, agarose, alginate, chitosan, dextran, gelatin, laminins, collagens, hyaluronan, fibrin, or mixtures thereof, or are selected from the group of complex tissue-derived matrices consisting of Matrigel, Myogel and Cartigel, wherein the concentration of collagen in the hydrogel is between 0.4 mg/ml and about 3.6 mg/ml and Matrigel is at a percentage between 90% (v/v) and 10% (v/v); or ii. a crosslinked synthetic hydrophilic polymer functionalized with an extracellular matrix (ECM)-derived protein or peptide, wherein the hydrophilic polymer is selected from the group comprising: poly(ethylene glycol), polyoxazoline, polyaliphatic polyurethanes, polyether polyurethanes, polyester polyurethanes, polyethylene copolymers, polyamides, polyvinyl alcohols, poly(ethylene oxide), polypropylene oxide, polypropylene glycol, polytetramethylene oxide, polyvinyl pyrrolidone, polyacrylamide, poly(hydroxy ethyl acrylate), poly(hydroxyethyl methacrylate) and mixtures or co-polymers thereof; or iii. a combination of naturally delivered and synthetic precursors;

wherein supportive cells are cultured inside the hydrogel, the supportive cells are selected from the group comprising fibroblasts, myoblasts, myofibroblasts, endothelial cells and/or cells of the immune system.

5. The method of claim 1, wherein the stem cells form a tissue-like colony, the tissue-like colony comprises an epithelial-like tissue.

6. An organoid produced by the method of claim 1.

7. An array of the organoids of claim 6 within a 2D plane, preferably wherein:

i. the organoids are equally spaced within the array, preferably wherein the space between adjacent organoids in the array is equal to or greater than the length of any of the adjacent organoids within the plane of the array, ii. the size of the array is between 10 μm to 100 mm in width and/or length, and iii. the array is folded to form a 3D shape, preferably a tube.

8. The method of claim 1, wherein one principal axis is longer than the other principal axis.

9. The method of claim 5, wherein the epithelial-like tissue comprises a lumenized multicellular structure.

10. The method of claim 5, wherein the tissue-like colony comprises an accessible epithelium.

*    *    *    *    *